United States Patent [19]

Yamashita et al.

[11] Patent Number: 5,224,035
[45] Date of Patent: Jun. 29, 1993

[54] METHOD AND APPARATUS FOR JUDGING DEFORMATION OF VERTEBRAL BODY

[75] Inventors: Gentaro Yamashita, Tachikawa; Yasuhiro Uotani, Koshigaya; Choju Aoki, Kawasaki, all of Japan

[73] Assignee: Teijin Limited, Osaka, Japan

[21] Appl. No.: 873,900

[22] Filed: Apr. 24, 1992

Related U.S. Application Data

[63] Continuation of Ser. No. 541,173, Jun. 20, 1990, abandoned, which is a continuation of Ser. No. 46,751, May 7, 1987, abandoned.

[30] Foreign Application Priority Data

May 7, 1986 [JP] Japan ................................ 61-103198
Jul. 31, 1986 [JP] Japan ................................ 61-178882

[51] Int. Cl.[5] ............................................. G06F 15/42
[52] U.S. Cl. .............................................. 364/413.02
[58] Field of Search ................................... 364/413.02

[56] References Cited

FOREIGN PATENT DOCUMENTS 0069229 1/1983 European Pat. Off. .

OTHER PUBLICATIONS

"Computer Assessment of Vertebral Deformity (Report 1)"; Deguchi et al., *JBMM* vol. 6, No. 2, Aug. 1988, pp. 21-28.

European Search Report, EP 87304069.
Medical and Biological Engineering and Computing, vol. 20, No. 6, Nov. 1982, pp. 715-726, Stevenage, Harts, GB; J. Koreska et al.: "Portable desktop computer-aided digitiser system for the analysis of spinal deformaties".
B. L. Riggs et al "Effect of the Fluoride/Calcium Regimen on Vertebral—" pp. 446-450, The New England Journal of Medicine Feb. 25, 1982.
B. E. C. Nordin "Calcium, Phosphate and Magnesium Metabolism" (1976) pp. 374-379, 576-578.

*Primary Examiner*—Stephen M. Baker
*Attorney, Agent, or Firm*—Sughrue, Mion, Zinn, Macpeak & Seas

[57] ABSTRACT

A method for judging deformation of a vertebral body includes the steps of measuring a central length (a), rear brim length (c), and front brim length (d) from a profile X-ray image of a vertebral body to be judged, determining ratios of c/d, a/c and a/d, and classifying deformation of the vertebral body to be judged by using indices, c, d, c/d, a/c and a/d. Furthermore, a method for judging deformation of a vertebral body, which comprises obtaining at least two indices by measuring a central length (a), vertebral body width (b), rear brim length (c), and front brim length (d) from a profile X-ray image of a vertebral body, analyzing these indices by a discriminant function, and classifying a deformation of the vertebral body from results of the analysis.

17 Claims, 7 Drawing Sheets

Fig. 3
NO DEFOMATION
WEDGE-SHAPED VERTEBRAL
FISH VERTEBRAL
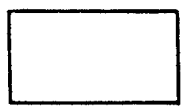
FLAT VERTEBRAL
INVERSE WEDGE-SHAPED VERTEBRAL
Fig. 4
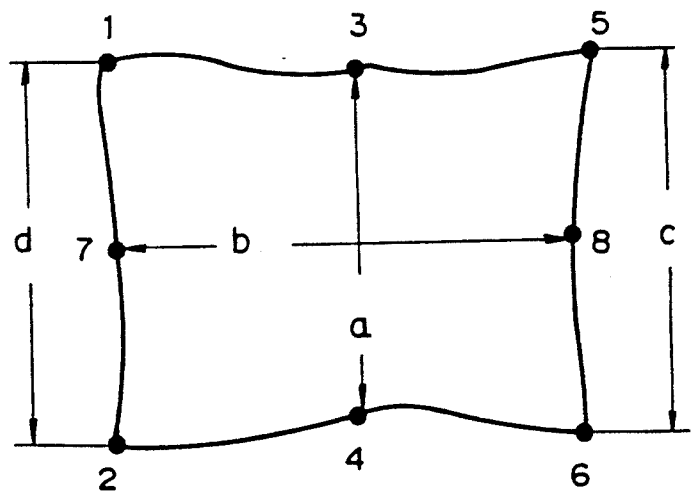

METHOD AND APPARATUS FOR JUDGING DEFORMATION OF VERTEBRAL BODY

This is a continuation of application Ser. No. 07/541,173 filed Jun. 20, 1990, which is a continuation of application Ser. No. 07/046,751 filed May 7, 1987, both now abandoned.

BACKGROUND OF THE INVENTION

1. Field of the Invention

The present invention relates to a method and apparatus for judging deformation of a vertebral body. More particularly, the present invention relates to a method and apparatus for judging deformation of a vertebral body which is one of the bones forming the spinal column. A judgment of the presence of vertebral body deformation accompanied by osteoporosis, as well as a classification of the deformation, is very important for grasping the progress of osteoporosis and for confirmation of the effect of therapy.

2. Description of the Related Art

In the prior art, the presence of deformation of a vertebral body which is one of the bones forming the spinal column has been judged by a physician by visual observation of the profile X-ray images of thoracic vertebrae or lumbar vertebrae. However, compared with a fracture of the so called long bones such as the femur, tibia, radius, ulna, etc., a judgment of vertebral deformation is difficult since this is usually a wedge-shaped deformation, pressure fracture, depressed fracture, etc., and any judgment inevitably involves individual differences. Also, even if an attempt is made to monitor changes over a period of time, for confirmation of the effect of therapy, because the deformation cannot be quantified, progress of the deformation, if any, cannot be easily determined.

Also, although a method has been reported in which the ratio (a/d) of the central length (a) to the front brim length (d) of the third lumbar vertebrae is determined as the index (Lumbar Spine Score) for the degree of bone atrophy, or a change in the longitudinal and lateral bone beams of the third lumbar vertebrae is observed as the index for the degree of bone atrophy (severity classified by Jikei University), or a judgment of the fracture of a vertebral body is made by measurement of the central length (a), front brim length (d) and rear brim length (c) of a vertebral body *The New England Journal of Medicine*, vol. 306, 446 (Feb. 25, 1982), a method for classifying the type of deformation of a vertebral body has not heretofore been known.

SUMMARY OF THE INVENTION

Accordingly, the objects of the present invention are to eliminate the above-mentioned disadvantages of the prior art and to provide a method for objectively judging deformation of a vertebral body.

Other objects and advantages of the present invention will be apparent from the following description.

In accordance with the present invention, there is provided a method for judging deformation of a vertebral body, which comprises measuring a central length (a), a rear brim length (c), and front brim length (d) from a profile X-ray image of a vertebral body to be judged, determining ratios of c/d, a/c, and a/d, and classifying deformation of the vertebral body to be judged by using indices, c, d, c/d, a/c and a/d.

In accordance with the present invention, there is also provided a method for judging deformation of a vertebral body, which comprises obtaining at least two indices by measuring a central length (a), vertebral body width (b), rear brim length (c), and front brim length (a) from a profile X-ray image of a vertebral body, analyzing these indices by discriminant function and classifying a deformation of the vertebral body from results of said analysis.

In accordance with the present invention, there is further provided an apparatus for judging deformation of a vertebral body comprising (i) an input means for inputting at least two values of a central length (a), vertebral body width (b), rear brim length (c), and front brim length (d) from a profile X-ray image of a vertebral body to be judged, (ii) an arithmetic means for operating the calculation necessary for discriminating "wedge-shaped vertebrae", "inverse wedge-shaped vertebrae", "fish vertebrae", and "no deformation" to at least two types by using the above-mentioned input value, (iii) a means for discriminating the at least two types by using the calculation results, (iv) a means for inputting the discriminant function and/or standard necessary for the calculation and discrimination, and (v) an output means for outputting the judgment result.

BRIEF DESCRIPTION OF THE DRAWING

The present invention will be better understood from the description set forth below with reference to the accompanying drawings, in which:

FIG. 3 shows an example of vertebral body deformation;

FIG. 4 shows the front brim length, central length, rear brim length, and vertebral body width in a profile X-ray image of a vertebral body;

DESCRIPTION OF THE PREFERRED EMBODIMENT

Figure 1:
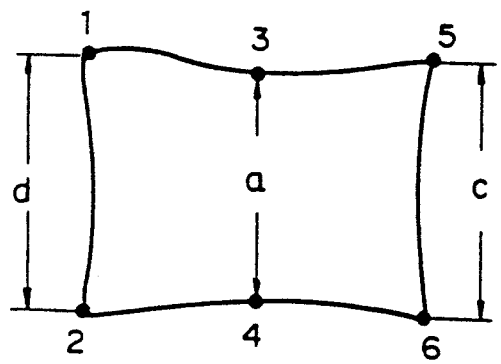
FIG. 1 shows a profile X-ray image of a vertebral body.

The present inventors have made an intensive study of a method of objective evaluation of vertebral body deformation, and found that the presence of a vertebral body deformation can be objectively judged using a standard in which lengths of the vertebral body and their ratios are combined by accurately measuring the lengths of a front brim, rear brim, central portion from a profile X-ray image (i.e., an image on a film taken from the side by X-ray radiation) of a vertebral body and determining the ratios of the respective portions of the vertebral body. The present inventors names and further found that the type of vertebral body deformation can be judged according to the standard lengths of the vertebral body and their ratios are, and the progress over a period of time of the vertebral body deformation can be judged from the change in the deformation type as well as a change in the lengths of the vertebral body. In view of the above findings, the inventors accomplished the present invention.

In the prior art, the profile X-ray image of vertebral body was visually observed by a physician in order to determine vertebral body deformation, but according to the present invention, the lengths of the respective portions of the vertebral body are measured, judgment standards are prepared with reference to a judgment by a physician, and the presence of vertebral body deformation as well as a classification of the deformation type are objectively performed following the judgment standards.

The judgment method of the present invention is now described in more detail.

(i) First, from a profile X-ray of a vertebral body without deformation, the central length (a), rear brim length (c), and front brim length (d) of each vertebral body are measured to determine an average value ($\bar{c}$) of c, an average value ($\bar{d}$) of d, and a standard deviation ($\sigma_c$, $\sigma_d$).

The above measurement is used to obtain standard values which become the judgment standard for the central length (a), rear brim length (c), and front brim length (d), etc., determined from a patient whose vertebral body deformation is to be judged.

The vertebral body without deformation to be measured is preferably a vertebral body of a person of from 50 to 75 years old, in view of the age of the patient whose vertebral body deformation is to be judged. Also, it is preferable to perform measurements separately for men and women, and it is desirable to perform measurements of about 50 vertebral bodies, or more, for both men and women.

When making a profile X-ray image of a vertebral body, the thoracic vertebrae from the first thoracic vertebrae to the twelfth thoracic vertebrae, lumbar vertebrae from the first lumbar vertebrae to the fifth lumbar vertebrae should be included, giving a total of 17 vertebral bodies, and therefore, for example, it is advantageous to take the photograph of the profile X-ray image with the eighth thoracic vertebrae as the center separately from the profile X-ray image with the third lumbar vertebrae as the center. In the profile X-ray image with the eighth thoracic vertebrae as the center, the first thoracic vertebrae cannot be accurately measured in most cases, and further, the second and the third thoracic vertebrae are unclear in many cases. However, since the frequency of vertebral body deformation is not great in these vertebral bodies, it is sufficient if measurement can be made from the fourth thoracic vertebrae or the fifth thoracic vertebrae.

The center length (a), rear brim length (c), and front brim length (d) of a vertebral body are specifically as shown in FIG. 1. For determination of these values, for the profile X-ray image of a vertebral body, the central length (a), rear brim length (c), and front brim length (d) may be measured for each vertebral body with a scale or slide calipers, but the six points of 1 to 6 shown in FIG. 1 can be input through a digitizer into a computer to measure the central length (a) (3-4), rear brim length (c) (5-6), and front brim length (d) (1-2), and to calculate the ratios of c/d, a/c, a/d. Also, for example, the degree of blackening may be recorded with a TV camera, etc., and the lengths of the respective portions of the vertebral body may be automatically measured by image processing.

(ii) Subsequently, from the profile X-ray image of the vertebral body of the patient whose vertebral body deformation is to be judged, as in (i), the center length (a), rear brim length (c), and front brim length (d) of each vertebral body are measured, and further, the ratios of c/d, a/c and a/d are determined by calculation.

These measurements can be conducted exactly as in the case of the above (i).

(iii) Next, a judgment of vertebral body deformation can be made from a, c, d, c/d, a/c and a/d, for example, as follows.

That is, (A) when c/d, c, d, a/c, a/d satisfy the following conditions, the judgment can be "no deformation" (type N):

(a) $0.7 < c/d < 1.4$;

(b) at least one of $c \geq \bar{c} - 2\sigma$ and $d \geq \bar{d} - 1.5\sigma_d$ is satisfied; and (c) at least one of $a/c > 0.8$ and $a/d > 0.8$ is satisfied.

As the judgment standard for such "no deformation", the ratio c/d of the rear brim length to the front brim length must be between 0.7 and 1.4 as the first condition (a). For, as described below, if c/d becomes 1.4 or more, the front brim portion becomes a deformed wedge-shaped vertebrae, and if c/d becomes 0.7 or less, the rear brim portion becomes a deformed inverse wedge-shaped vertebrae, which in practice is very rare.

Next, as the second condition (b), at least one of rear brim length c and front brim length d must be greater than $\bar{c} - 2\sigma_c$ and $\bar{d} - 1.5\sigma_d$ when the average values of the rear brim length c and front brim length d of vertebral body without deformation determined in (i) are made $\bar{c}$ and $\bar{d}$, respectively. In a typical healthy vertebral body, a, c, d all have a high value, namely $a \geq \bar{a} - 2\sigma_a$, $c \geq \bar{c} - 2\sigma_c$, $d \geq \bar{d} - 1.5\sigma_d$, but even when the vertebral body is slightly compressed to become $a \geq \bar{a} - 2\sigma_a$, provided that at least one of the conditions of $c \geq \bar{c} - 2\sigma_c$ or $d \geq \bar{d} - 1.5\sigma_d$, can be satisfied, no clear vertebral body deformation is recognized and judgment of "no deformation" may be made.

As the third condition, at least one of a/c and a/d must be more than 0.8. For, if both of a/c and a/d are 0.8 or less, namely the center length a is much smaller than the rear brim length c and front brim length d, a fish vertebrae condition as described below is determined.

Thus, for the above reasons, when the above conditions of (a), (b) and (c) are satisfied, a judgment of "no deformation" can be made.

Figure 2:
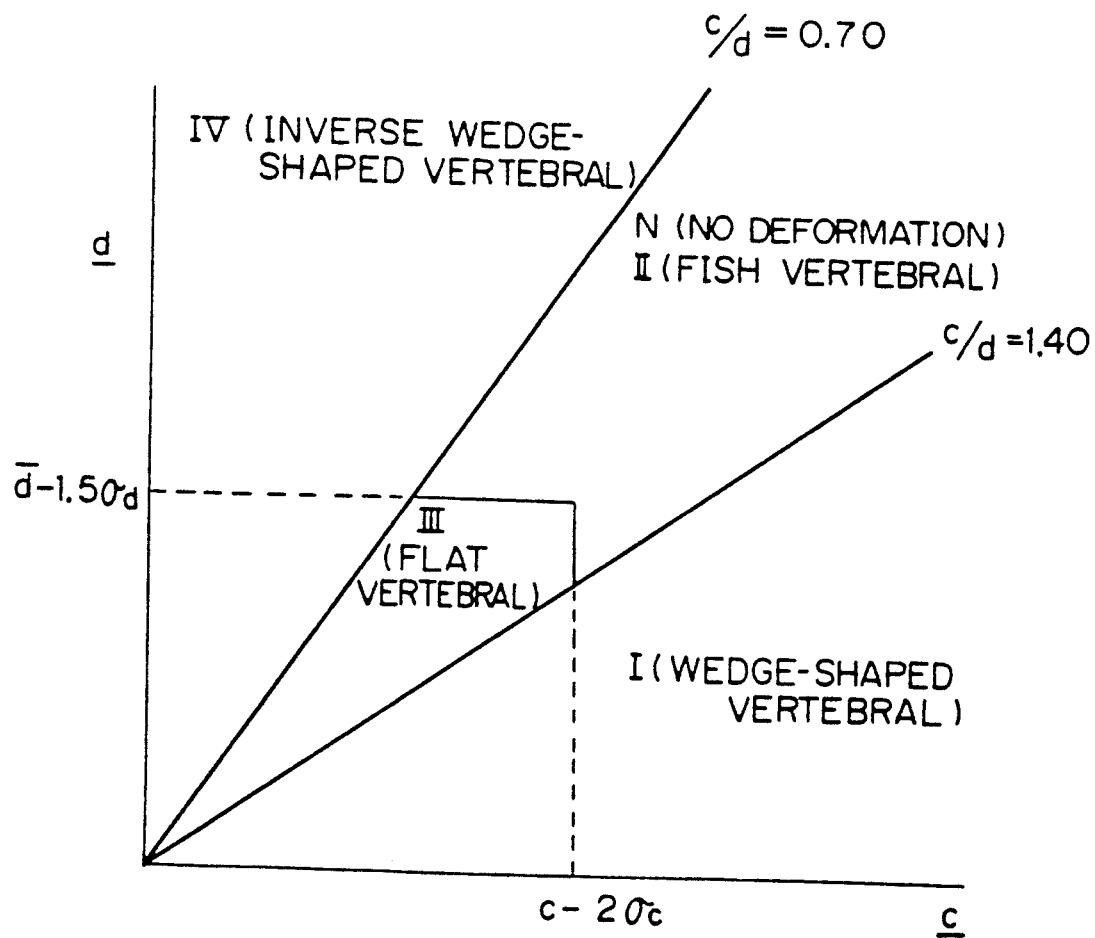
FIG. 2 shows the relationships of the respective vertebral body deformations and front brim length (d), rear brim length (c), etc., according to the judgment method of the present invention.
Figure 5:
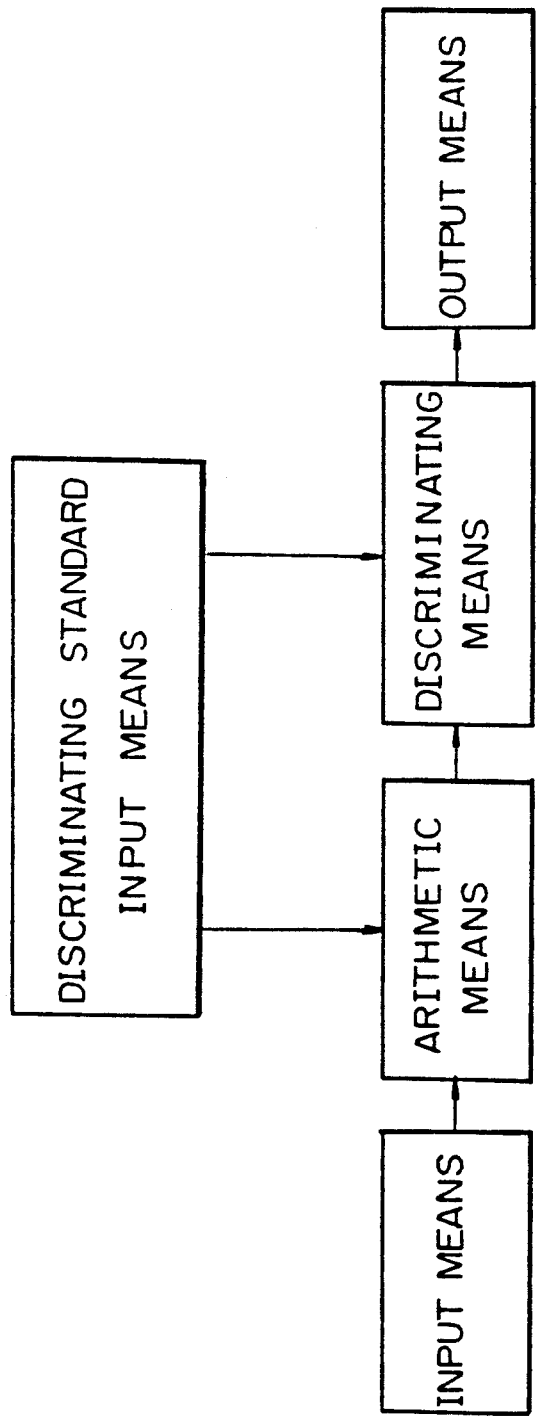
FIG. 5 is a block diagram illustrating the basic structure of an apparatus for judging deformation of a vertebral body by using an X-ray image of the vertebral body.
Figure 6:
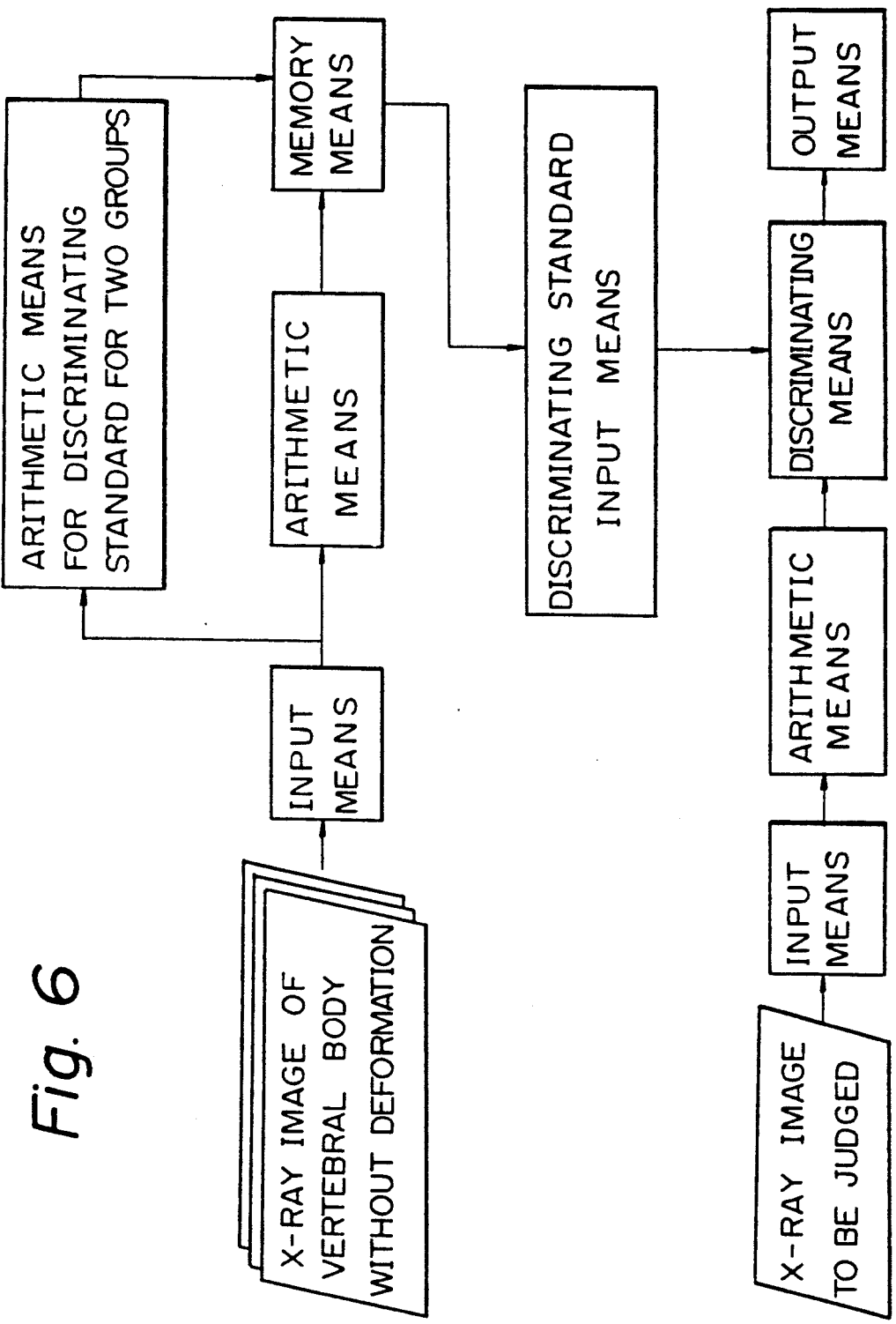
FIG. 6 is a block diagram illustrating an apparatus for judging deformation of a vertebral body in the X-ray image of the vertebral body to be judged by using a discriminating standard obtained mainly from X-ray images of vertebral bodies having no substantial deformation, in which a means for inputting information relating to X-ray images of vertebral bodies having deformation caused therein is further required.
Figure 7:
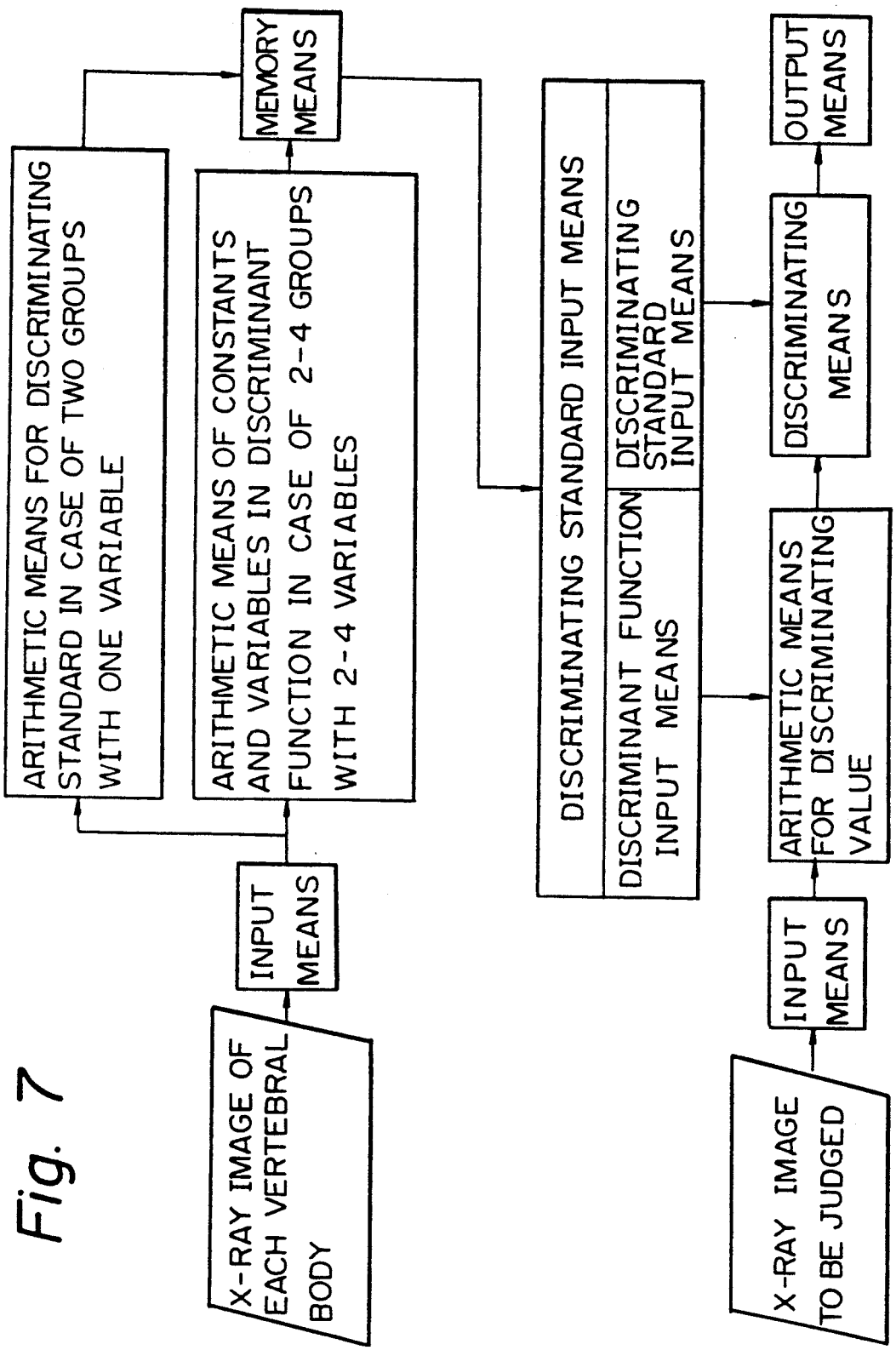
FIG. 7 is a block diagram illustrating an apparatus for judging deformation of a vertebral body by using, as a criteria, a discriminating standard obtained by mainly using a discriminating function.
Figure 8:
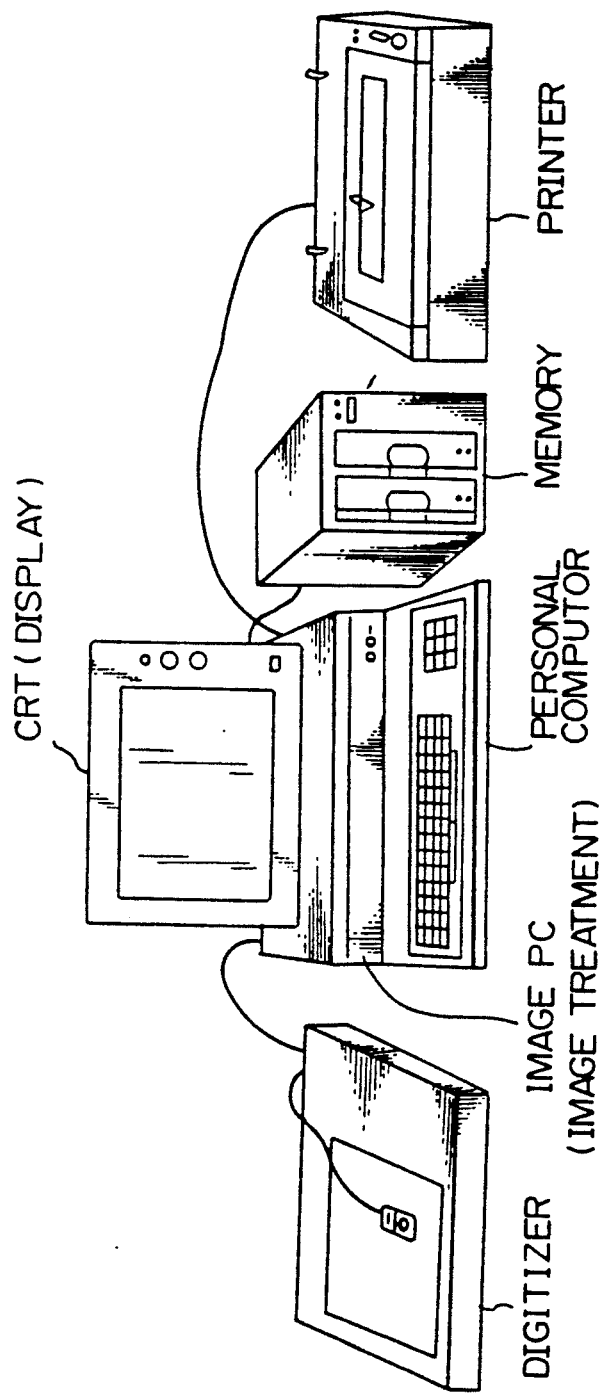
FIG. 8 shows an apparatus for judging deformation of a vertebral body comprising a digitizer for inputting the points 1 to 6 in FIG. 1 or the points 1 to 8 in FIG. 4 from the X-ray image to a computer; a personal computor for classifying the presence or absent of the deformation and types of the deformation by measuring the lengths a, c, and d in FIG. 1 or a, b, c, and d in FIG. 4, followed by the image treatment; a memory including a software for effecting the above-mentioned treatment; and a printer for printing out, for example, the measured values or the types of deformation.
Figure 9:
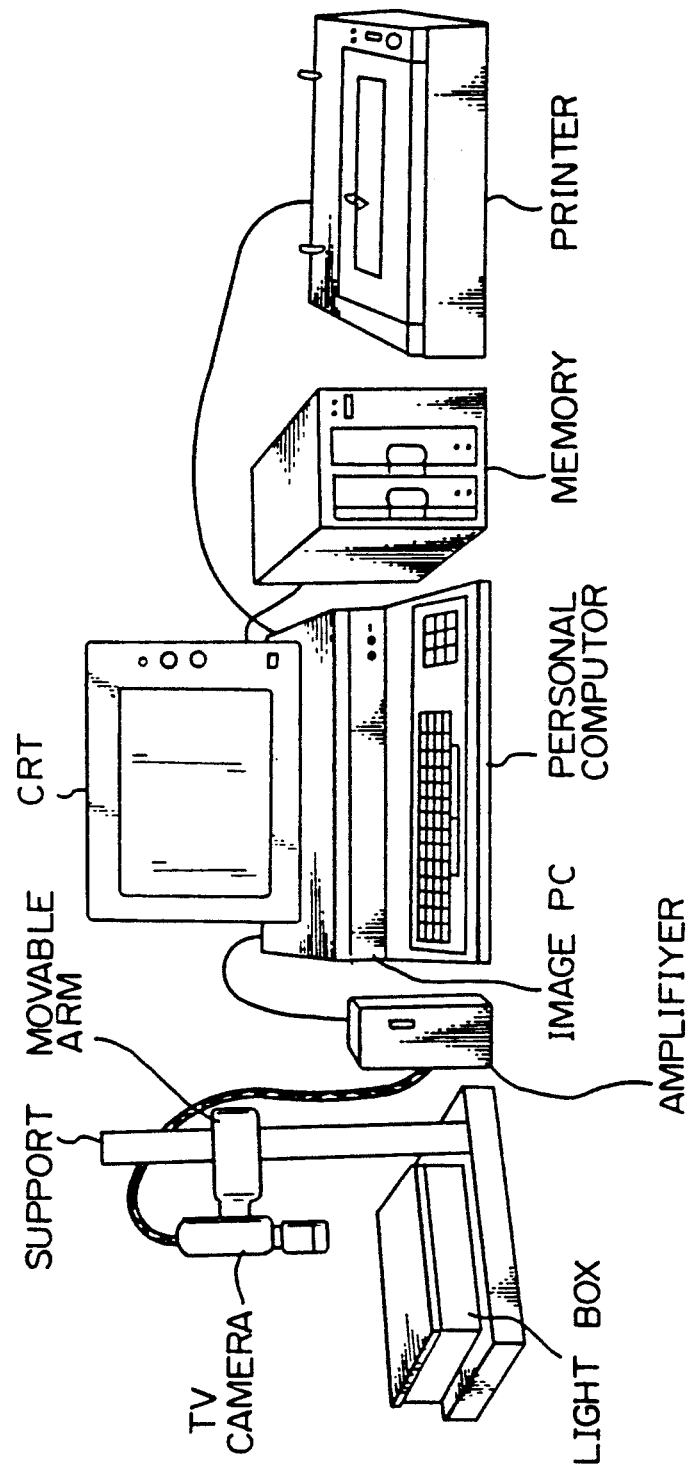
FIG. 9 shows an apparatus for judging deformation of a vertebral body comprising a TV camera for reading the image of each vertebral body from the X-ray image; a personal computer for classifying the presence or absence of the deformation and the types of the deformation by measuring the lengths a, c, and d in FIG. 1 or the lengths a, b, c, and d in FIG. 4 from the read X-ray image; a including a software for registering the above images and effecting the above-mentioned treatment.

The relationship of the conditions of (a), (b), and (c), or the respective conditions as described below with the respective types of vertebral body deformation, including "no deformation", are shown in FIG. 2.

(B) When c/d≧1.4, the judgment can be a "wedge-shaped vertebrae" (type I).

In the wedge-shaped vertebrae, deformation has occurred at the front brim portion as shown in FIG. 3, and the front brim length (d) has become much smaller than the rear brim length (c). For example, when the front brim length is ¾ of the rear brim length (c/d=1.33), a wedge-shaped vertebral body deformation can be easily recognized, but in some cases, a clear wedge-shaped vertebrae cannot be easily recognized. On the other hand, when the front brim length is ⅔ of the rear brim length (c/d=1.5), it can be clearly recognized as a wedge-shaped vertebrae, and therefore, c/d≧1.4 is made the judgment standard for wedge-shaped vertebrae.

In addition to the so called wedge-shaped vertebrae, the wedge-shaped vertebrae (type I) is inclusive of deformations with shortened front brim length, like a wedge-shaped vertebrae, as a result of, for example, an upper brim pressure fracture, upper brim depressed fracture, lower brim pressure fracture, lower brim depressed fracture, and as described below, even in the case of a vertebral body which is judged as a flat vertebrae because $a < \bar{a} - 2\sigma_a$, $c < \bar{c} - 2\sigma_c$, $d < \bar{d} - 1.5\sigma_d$, if there is a remarkable deformation at the front brim portion satisfying c/d≧1.4, it can be judged to be a wedge-shaped vertebrae.

(C) When c/d≦0.7, the judgment can be an "inverse wedge-shaped vertebrae" (type IV).

The inverse wedge-shaped vertebrae may be defined as a vertebral body wherein deformation has occurred at the rear brim portion, and thus the rear brim length (c) has become smaller than the front brim length (d), contrary to the wedge-shaped vertebrae wherein deformation has occurred at the front brim portion, and the front length (d) has become smaller than the rear brim length (c) (see FIG. 3), but in practice, such a vertebral body does not substantially exist. In the fifth lumbar vertebrae, as shown in Example 1, the rear brim length (c) is smaller than the front brim length (d), with the average value of c/d being lower than 1, e.g., 0.95, but in some cases, an inverse wedge-shaped vertebrae cannot be clearly recognized even when the rear brim length (c) is ¾ of the front brim length (d) (c/d=0.75), and therefore, a judgment of an inverse wedge-shaped vertebrae (type IV) can be made when c/d≦0.7.

(D) When c, d, c/d satisfy the conditions shown below, the judgment can be a "flat vertebrae" (type III):

(a) $c < \bar{c} - 2\sigma_c$;
(b) $d < \bar{d} - 1.5\pi_d$; and
(c) 0.7 < c/d < 1.4.

In the first condition (a) and the second condition (b), the rear brim length (c) and the front brim length (d) are both smaller than $\bar{c} - 2\sigma_c$ and $\bar{d} - 1.5\sigma_d$ when the average values of the vertebral body without deformation are made $\bar{c}$ and $\bar{d}$; namely, $c < \bar{c} - 2\sigma_c$ and $d < \bar{d} - 1.5\sigma_d$.

The flat vertebrae is a vertebral body having a relatively uniform deformation at the front brim portion, the central portion, and the rear brim portion under pressure (see FIG. 3); namely, all of the front brim length (d), the central length (a) and the rear brim length (c) are smaller. As shown by the average values of the lengths of the respective portions of the vertebral body without deformation of Example 1, since the central length (a) is smaller than the front brim length (d) or the rear brim length (c) even in the vertebral body without deformation, the specific feature of the flat vertebrae resides in a particularly small front brim length (d) and rear brim length (c), and the vertebral body wherein $c < \bar{c} - 2\sigma_c$ and $d < \bar{d} - 1.5\sigma_d$ is judged to be a flat vertebrae (type III). The conditions of $-2\sigma_c$ for C and $-1.5\sigma_d$ for D are set because $\bar{c}$ is greater than $\bar{d}$ ($\bar{c} > \bar{d}$) as shown in Example 1, and thus C and D become approximately equal values by setting such conditions, to satisfy the conditions for a flat vertebrae. The third condition (c) is 0.7 < c/d < 1.4. For, even where $a < \bar{a} - 2\sigma_a$, $c < \bar{c} - 2\sigma_c$, $d < \bar{d} - 1.5\sigma_d$, deformation at the front brim portion is particularly marked, and where c/d ≧ 1.4, it can be judged to be a wedge-shaped vertebrae, while in the case of a marked deformation at the rear brim portion when c/d ≦ 0.7, it is judged to be an inverse wedge-shaped vertebrae.

(E) When c/d, c, d, a/c, a/d satisfy the following conditions, the judgment can be a "fish vertebrae" (type II):

(a) 0.7 < c/d < 1.4;
(b) at least one of $c \geq \bar{c} - 2\sigma_c$ and $d \geq \bar{d} - 1.5\sigma_d$ is satisfied;
(c) a/c ≦ 0.8 and a/d ≦ 0.8.

"Fish vertebrae" is a vertebrae where a depressed fracture or a pressure fracture has occurred at the central portion, whereby the central length (a) is particularly smaller than the front brim length (d) and rear brim length (c) (see FIG. 3). Accordingly, among the so called "no deformation" classifications, except for wedge-shaped vertebrae, flat vertebrae, and inverse wedge-shaped vertebrae, the central length (a) is particularly smaller. When the central length (a) is smaller than the front brim length (d) and the rear brim length (c), thus satisfying a/c < 0.9 and a/d < 0.9, deformation such as fish vertebrae can be clearly recognized, but in some cases a clear fish vertebrae cannot be recognized, and therefore, a/c < 0.8 and a/c < 0.8 can be made the judgment standards for fish vertebrae.

In addition to the so called fish vertebrae, the fish vertebrae (type II) is also inclusive of deformations with a shortened central length like fish vertebrae, as a result of an upper brim pressure fracture, upper brim depressed fracture, lower brim pressure fracture, lower brim depressed fracture, etc.

The relationships between these judgment standards for "no deformation", "wedge-shaped vertebrae", "inverse wedge-shaped vertebrae", "flat vertebrae" and "fish vertebrae", are shown in FIG. 2.

In the judgment as described above, explanation has been made by selecting the upper limit as 1.4 and the lower limit as 0.7 as the judgment standard for c/d as a preferable example, but these values can be selected freely, for example, in the case of the upper limit, from the range of 1.25 to 1.55, preferably from 1.33 to 1.5, more preferably from 1.4 to 1.45. The lower limit can be selected freely from the range of 0.8 to 0.6, preferably from 0.75 to 0.65.

As the judgment standard for a/c and a/d, 0.8 was selected in the case of "no deformation" and "fish vertebrae", but this value can be freely selected from the range of 0.65 to 0.9, preferably from 0.7 to 0.85, more preferably from 0.75 to 0.8.

As the judgment standard for c and d, $\bar{c}-2\sigma_c$ and $\bar{d}-1.5\sigma_d$ were selected in the case of "no deformation", "flat vertebrae", and "fish vertebrae" but the judgment standard for c can be freely selected from the range of $\bar{c}-1.0\sigma_c$ to $\bar{c}-2.5\sigma_c$, preferably $\bar{c}-1.25\sigma_c$ to $\bar{c}-2.25\sigma_c$, more preferably $\bar{c}-1.5\sigma_c$ to $\bar{c}-2.0\sigma_c$. The judgment standard for d also can be similarly selected from the range of $\bar{d}-1.0\sigma_d$ to $\bar{d}-2.5\sigma_d$, preferably $\bar{d}-1.25\sigma_d$ to $\bar{d}-2.25\sigma_d$, more preferably $\bar{d}-1.5\sigma_d$ to $\bar{d}-2.0\sigma_d$.

As mentioned above, although the coefficients $\beta_1$ to $\beta_6$ can be previously set in the present invention, $\beta_1$ to $\beta_6$ may optionally be determined from a discriminating function capable of discriminating two groups with two variants or two groups with one variant by using values obtained by measuring two of a, b, c and d, with respect to at least five profile X-ray image in each of two types among four types (i.e., wedge-shaped vertabrae, fish vertabrae flat vertebral, and no deformation). As typical examples, $\beta_1$ is $z_5$ obtained by the following discriminant function using the ratio c/d derived from c and d, which are obtained by measuring at least five profile X-ray images in each of two types selected from "wedge-shaped vertebrae" and "no deformation":

(i) When the standard deviation $\sigma_1$ of c/d of at least five profile X-ray image of "wedge-type vertebrae" is substantially the same as the standard deviation $\sigma_2$ of c/d of at least five profile X-ray images of "no deformation".

$$z_5 = \mu + \frac{\sigma^2}{\mu_1 - \mu_2} l_n \frac{\pi_2}{\pi_1}$$

wherein $\mu_1$ and $\mu_2$ are averages of c/d relating to the profile X-ray images of "wedge-shaped vertebrae" and "no deformation", respectively, $\pi_1$ and $\pi_2$ are numbers of the X-ray images of "wedge-type vertebrae" and "no deformation", respectively, $\mu$ is an average of $\mu_1$ and $\mu_2$, and $\sigma$ is an average of $\sigma_1$ and $\sigma_2$; and (ii) When $\sigma_1$ and $\sigma_2$ are substantially different, $$Z_5 = \frac{-B \pm \sqrt{B^2 - 4A \cdot C}}{2A}$$

$$A = \frac{1}{\sigma_2^2} - \frac{1}{\sigma_1^2}$$

$$B = -2\frac{\mu_2}{\sigma_2^2} - \frac{\mu_1}{\sigma_1^2}$$

$$C = \frac{\mu_2^2}{\sigma_2^2} - \frac{\mu_1^2}{\sigma_1^2} - 2 \cdot \log \frac{\pi_2}{\pi_1}$$

wherein $\mu_1$ and $\mu_2$ are averages of c/d relating to the profile X-ray images of "wedge-shaped vertebrae" and "no deformation", respectively, $\pi_1$ and $\pi_2$ are the number of the X-ray images of "wedge-type vertebrae" and "no deformation", respectively.

Furthermore, the present inventors have made an intensive study of a method of objective evaluation of vertebral body deformation, and found that the presence of a vertebral body deformation as well as the deformation type can be judged objectively by use of a discriminant function by accurately measuring the lengths of, for example, the front brim (d), rear brim (c), central portion (a), and the vertebral body width (b) from a profile X-ray image of a vertebral body, and further found that the progress over a period of time of the vertebral body deformation can be judged from the change in the type of said deformation as well as the change in the lengths of the vertebral body, and thus accomplished the present invention.

In the prior art, vertebral body deformation has been judged by a physician by visual observation of the profile X-ray image of a vertebral body, but according to the method of the present invention, the lengths of the respective portions of a vertebral body are measured and for the vertebral bodies judged by a physician to be "no deformation", "wedge-shaped vertebrae", "fish vertebrae", and "flat vertebrae", discrimination is made by discriminant functions to determine discriminant formulae for the respective types of vertebral body deformations, and thereafter, the presence of vertebral body deformation and the type of deformation are objectively judged by these discriminant formulae for a patient whose vertebral body deformation is to be judged.

The types of deformed vertebral bodies are classified in the present invention generally into wedge-shaped vertebrae, fish vertebrae, and flat vertebrae.

In the wedge-shaped vertebrae (type I), deformation has occurred at the front brim portion as shown in FIG. 4, and the front brim length has become particularly smaller than the rear brim length, including in addition to the so called wedge-shaped vertebrae deformation with a shortened front brim length like wedge-shaped vertebrae as the result of upper brim pressure fracture, an upper brim depressed fracture, lower brim pressure fracture, and lower brim depressed fracture, etc. In the fish vertebrae (type II), the depressed fracture or pressure fracture has occurred at the central portion, whereby the central length has become particularly smaller than the front brim length and rear brim length (see FIG. 4), including in addition to the so called fish vertebrae deformations with a shortened center length like fish vertebrae as the result of upper brim pressure fracture, an upper brim depressed fracture, lower brim pressure fracture, and lower brim depressed fracture, etc.

In the flat vertebrae (type III), the front brim portion, central portion, and rear brim portion are deformed relatively uniformly under pressure (see FIG. 4); namely, all of the front rear length, central length, and rear brim length are smaller.

In addition, there is the inverse wedge-shaped vertebrae (type IV). This type is defined as a vertebral body wherein deformation has occurred at the rear brim portion, and thus the rear brim length is smaller than the front brim length, contrary to the wedge-shaped vertebrae where deformation has occurred at the front brim portion, and the front brim portion is smaller than the rear brim length (see FIG. 4). In practice, however, such a vertebrae does not substantially exist. Accordingly, it is sufficient if the four types, wedge-shaped vertebrae, fish vertebrae, flat vertebrae and "no deformation", can be classified.

The judgment method of the second aspect of the present invention is now described in more detail.

(i) First, the vertebral body, central length (a), vertebral body width (b), rear brim length (c), and front brim length (d) of each of the vertebrae judged by a physician as "no deformation", wedge-shaped vertebrae, fish vertebrae and flat vertebrae, are measured from a profile X-ray of the vertebral body.

The above measurement is used to determine the discriminant formula for discriminating the presence of vertebral body deformation as well as the deformation type. Accordingly, the vertebral bodies of these respective types should be preferably vertebral bodies of persons generally 50 to 75 years old, in view of the age of the patient whose vertebral body deformation is to be judged. Also, it is preferable to perform measurements separately for men and women, and it is desirable to perform measurements of about fifty or more vertebral bodies for both men and women. However, since wedge-shaped, vertebrae, fish vertebrae and flat vertebrae do not widely occur, the discriminant formula for discrimination of the vertebral body deformation type according to the method of the present invention can be determined if at least five each of these deformed vertebral bodies can be measured.

Also, from the first to twelfth thoracic vertebrae and the first to the fifth lumbar vertebrae, the size differs for each vertebral body, and therefore, it is necessary to measure each vertebral body and determine each deformation type.

When making a profile X-ray image of a vertebral body, the thoracic vertebrae from the first thoracic vertebrae to the twelfth thoracic vertebrae, lumbar vertebrae from the first lumbar vertebrae to the fifth lumbar vertebrae should be included, giving a total of seventeen vertebral bodies, and therefore, for example, it is advantageous to take the photograph of the profile X-ray image with the eighth thoracic vertebrae as the center separately from the profile X-ray image with the third lumbar vertebrae as the center. In the profile X-ray image with the eighth thoracic vertebrae as the center, the first thoracic vertebrae cannot be accurately measured in most cases, and further, the second and the third thoracic vertebrae are unclear in many cases. However, since the frequency of vertebral body deformation is not great in these vertebral bodies, it is sufficient if measurement can be made from the fourth thoracic vertebrae or the fifth thoracic vertebrae.

The center length (a), width (b), rear brim length (c), and front brim length (d) of a vertebral body are specifically as shown in FIG. 4. For determination of these values, from the profile X-ray image of a vertebral body, the central length (a), width (b), rear brim length (c), and front brim length (d) may be measured for each vertebral body with a scale or slide calipers, but the eight points of 1 to 8 shown in FIG. 4 can be input through a digitizer into a computer to measure the central length (a) (3-4), width (b) (7-8), rear brim length (c) (5-6), and front brim length (d) (1-2). Also, for example, the degree of blackening may be recorded with a TV camera, etc., and the lengths of the respective portions of the vertebral body may be automatically measured by image processing.

(ii) Next, discriminant formula for discriminating "no deformation", wedge-shaped vertebrae, fish vertebrae, and flat vertebrae is determined. Such a discriminating analysis is described in, for example, Chuichi Okuno et al "Multivariate Analytical Method" (published by Nikkagiren); Chuichi Okuno et al "Overall Multivariate Analytical Method" (published by Nikkagiren); Koichi Sugiyama "Introduction to Multivariate Data Analysis" (published by Asakura Shoten), and others, and calculation can be made by referring to these sublications. However, by inputting the central length (a), vertebral body width (b), rear brim length (c), and front brim length (d) of the respective deformation types determined in (i) by a commercially available computer program (e.g., BMD multivariate analysis program from IBM Co.), the discriminant formula for discriminating "no deformation", wedge-shaped vertebrae, fish vertebrae, and flat vertebrae can be simply obtained. Such discriment formulae are specifically described as follows. That is, the following formulae and the vertebral body is judged from the maximum value of $z_1$ to $z_4$:

$$z_1 = a_{10} + a_{11}x_1 + a_{12}x_2 + a_{13}x_3 + a_{14}x_4$$

$$z_2 = a_{20} + a_{21}x_1 + a_{22}x_2 + a_{23}x_3 + a_{24}x_4$$

$$z_3 = a_{30} + a_{31}x_1 + a_{32}x_2 + a_{33}x_3 + a_{34}x_4$$

$$z_4 = a_{40} + a_{41}x_1 + a_{42}x_2 + a_{43}x_3 + a_{44}x_4$$

wherein $z_1$, $z_2$, $z_3$, and $z_4$ are discriminant values of "wedge-shaped vertebrae", "fish vertebrae", "flat vertebrae", and "no deformation", respectively, $x_1$, $x_2$, $x_3$, and $x_4$ are variables corresponding to a central length, vertebral body width, rear brim length, and front brim length, respectively, $a_{10}$, $a_{20}$, $a_{30}$, and $a_{40}$ are constants, and $a_{11}$ to $a_{44}$ are coefficients. This discriminant formula must be determined for each vertebral body from the first thoracic vertebrae to the fifth lumbar vertebrae, generally from the fourth thoracic vertebrae to the fifth lumbar vertebrae. (iii) Next, from the profile X-ray image of the vertebral body of the patient whose vertebral body deformation is to be judged, the central length (a), vertebral body width (b), rear brim length (c), and front brim length (d) are measured for each vertebral body as described in (i), and by substituting a, b, c and d in the discriminant formula determined in (ii), the discriminant values for "no deformation", wedge-shape vertebrae, fish vertebrae, and flat vertebrae are determined respectively, and the type which has the highest numerical value is judged to be the vertebral body deformation type. For example, when the vertebral body deformation type of the third lumbar vertebrae of the patient is to be judged, the respective measured values of a, b, c and d are substituted in the discriminant formula of the third lumbar vertebrae determined in (ii) as a matter of course. Having described above the method for judging, the present invention is not limited to the above classification of the four vertebral deformation types of "no deformation", wedge-shaped vertebrae, fish vertebrae and flat vertebrae from the four measured values of central length (a), vertebral body width (b), rear brim length (c), and front brim length (d), but it is also possible to classify the vertebral body deformation types by use of the discriminant function as described below.

(A) Method for classifying the three vertebral body deformation types from three or four measured values.

For example, in the first to the eleventh thoracic vertebrae, in which fish vertebrae do not generally exist, classification is required for only the three types of "no deformation", wedge-shaped vertebrae, and flat vertebrae. It may also arise that sufficient measured values of a, b, c, and d of fish vertebrae cannot be obtained for determining the discriminant formula even if a classification of the four types including fish vertebrae is desired.

In such cases, it is possible to determine the discriminant formula for classifying the three types of "no deformation", wedge-shaped vertebrae, and flat vertebrae from the four measured values of the central length (a), vertebral body width (b), rear brim length (c), and front brim length (d), or from three of these four measured values, for example, three measured values of a, c, and d.

(B) Method for classifying two vertebral body deformation types from two to four measured values.

Fish vertebrae and flat vertebrae can be judged relatively easily even when visually observed, and rarely occur, and therefore, in some cases they are difficult to judge with the use of a discriminant formula. Accordingly, when it is desired to classify only "no deformation" and wedge-shaped vertebrae by use of a discriminant formula, three, for example, a, c and d, or two, for example, measured values of c and d, can be used to determine the discriminant formula.

Also, in such a case, it is possible to determine the discriminant value for classifying "no deformation" and wedge-shaped vertebrae by using a single variate discriminant function of c/d.

Specifically speaking, the discriminant function is represented by the following formula in which the ratio (c/d) of c and d measured from at least five profile X-ray images in each of two types of "wedge-shaped vertebrae" and "no deformation" and the ratio (c/d) of less than $z_5$ obtained from the vertebral body to be judged is judged as "no deformation" and the ratio (c/d) equal to or larger than $z_5$ is judged as "wedge-shaped vertebrae".

(i) When the standard deviation $\sigma hd\ 1$ of c/d of at least five profile X-ray image of "wedge-type vertebrae" is substantially the same as the standard deviation $\sigma_2$ of c/d of at least five profile X-ray images of "no deformation".

$$z_5 = \mu + \frac{\sigma^2}{\mu_1 - \mu_2} l_n \frac{\pi_2}{\pi_1}$$

wherein $\mu_1$ and $\mu_2$ are averages of c/d relating to the profile X-ray images of "wedge-shaped vertebrae" and "no deformation", respectively, $\pi_1$ and $\pi_2$ are numbers of the X-ray images of "wedge-type vertebrae" and "no deformation", respectively, $\mu$ is an average of $\mu_1$ and $\mu_2$, and $\mu$ is an average of $\sigma_1$ and $\sigma_2$; and (ii) When $\sigma_1$ and $\sigma_2$ are substantially different, $$z_5 = \frac{-B \pm \sqrt{B^2 - 4A \cdot C}}{2A}$$

$$A = \frac{1}{\sigma_2^2} - \frac{1}{\sigma_1^2}$$

$$B = -2 \frac{\mu_2}{\sigma_2^2} - \frac{\mu_1}{\sigma_1^2}$$

$$C = \frac{\mu_2^2}{\sigma_2^2} - \frac{\mu_1^2}{\sigma_1^2} - 2 \cdot \log \frac{\pi_2}{\pi_1}$$

wherein $\mu_1$ and $\mu_2$ are averages of c/d relating to the profile X-ray images of "wedge-shaped vertebrae" and "no deformation", respectively, $\pi_1$ and $\pi_2$ are numbers of the X-ray images of "wedge-type vertebrae" and "no deformation", respectively.

The apparatus for judging the deformation of vertebral body according to the present invention is used for the practice of the above-mentioned method of the present invention. This apparatus is basically composed of an inputting means for at least two indices of a, b, c, and d, an arithmetic means for effecting necessary operations for the discrimination, a discriminating means by using the calculation results, a means for inputting the discriminant function and/or standard necessary for the calculation and discrimination, and an output means for outputting the judgment result.

As the inputting means, a rule means, a digitizer means, an image processing means in which an image inputting means such as a TV camera is used.

In the preferred embodiment of the present apparatus, c/d, a/c, and a/d are determined by the arithmetic means, and $\bar{c}$, $\bar{d}$, $\sigma_c$, $\sigma_d$, and $\beta_1 - \beta_6$ are inputted as discriminating standards by the discriminating standard inputting means, and the discriminating means can discriminate the results by these standards. Furthermore, the present apparatus can be further provided with a means for obtaining the discriminating standards from a number of the profile X-ray images having no substantial deformation. Furthermore, the present apparatus can be optionally provided with an arithmetic means capable of discriminating two groups with two variants, which are used for determining the indices $\beta_1$ to $\beta_6$, or of discriminating two groups with one variant. In this case, the data of at least two types of the four types of the vertebral body, i.e., "wedge-shaped vertebrae", "fish vertebrae", "flat vertebrae", and "no deformation" should be input.

In another preferred embodiment of the present apparatus, the arithmetic means is connected to a discriminating standard input means for inputting the discriminant function, whereby the arithmetic means calculates the discriminating values with said discriminant function and the discriminating means determine the type of the vertebral body based on the maximum discriminating value. In this case, the present apparatus is provided with a function capable of discriminating the four types of the vertebral body, "wedge-shaped vertebrae", "fish vertebrae", "flat vertebrae", and "no deformation" from four one-dimensional formulas containing a total of four variables a, b, c and d. Furthermore, there is also the apparatus which is capable of judging the two types of the vertebral body with one variant.

According to the first aspect of the judgment method and the apparatus of the present invention, the type of vertebral body deformation can be objectively evaluated, and also the change in the said deformation type and the progress over a period of time of the vertebral body deformation can be judged.

Also, the present method and apparatus is very useful for determining the progress of bone disease such as osteoporosis, etc., and for confirmation of the effect of therapy.

According to the second aspect of the judgment method and apparatus of the present invention, the type of vertebral body deformation can be objectively evaluated, and further the change in the type of deformation type and the progress over a period of time of the vertebral body deformation can be judged.

Also, the present method and apparatus is very useful for determining the progress of bone disease such as osteoporosis, etc., and for confirmation of the effect of therapy.

respective vertebral bodies of the measured values of a, b, c and d, and the calculated values of c/d, are as shown in Table 1.

TABLE 1

| Site | | Data number | a | | b | | c | | d | | c/d Unit: mm | |
|---|---|---|---|---|---|---|---|---|---|---|---|---|
| | | | $\bar{x}$ | $\sigma$ | $\bar{x}$ | $\sigma$ | $\bar{x}$ | $\sigma$ | $\bar{x}$ | $\sigma$ | $\bar{x}$ | $\sigma$ |
| 2nd | thoracic vertebrae | 11 | 18.27 | 3.02 | 25.40 | 4.03 | 21.60 | 3.80 | 18.69 | 2.97 | 1.15 | 0.11 |
| 3rd | thoracic vertebrae | 56 | 17.08 | 2.20 | 25.30 | 2.67 | 21.03 | 2.44 | 18.46 | 2.10 | 1.14 | 0.11 |
| 4th | thoracic vertebrae | 141 | 17.83 | 2.25 | 26.65 | 2.60 | 21.28 | 2.17 | 18.41 | 2.07 | 1.16 | 0.10 |
| 5th | thoracic vertebrae | 194 | 18.20 | 2.12 | 27.22 | 2.52 | 21.74 | 2.21 | 18.62 | 2.05 | 1.17 | 0.09 |
| 6th | thoracic vertebrae | 210 | 18.87 | 1.90 | 28.31 | 2.70 | 22.02 | 1.81 | 18.67 | 2.02 | 1.18 | 0.11 |
| 7th | thoracic vertebrae | 210 | 19.28 | 1.77 | 29.57 | 2.64 | 22.49 | 1.95 | 18.99 | 2.12 | 1.19 | 0.11 |
| 8th | thoracic vertebrae | 207 | 19.78 | 1.69 | 30.79 | 2.75 | 22.92 | 1.88 | 19.74 | 2.05 | 1.16 | 0.13 |
| 9th | thoracic vertebrae | 220 | 20.07 | 1.99 | 31.78 | 2.95 | 23.30 | 1.88 | 20.52 | 2.19 | 1.14 | 0.10 |
| 10th | thoracic vertebrae | 229 | 21.03 | 2.07 | 32.89 | 3.19 | 24.32 | 2.21 | 21.44 | 2.22 | 1.14 | 0.10 |
| 11th | thoracic vertebrae | 214 | 22.04 | 2.42 | 33.83 | 3.06 | 26.11 | 2.57 | 22.25 | 2.37 | 1.18 | 0.11 |
| 12th | thoracic vertebrae | 194 | 24.16 | 2.22 | 34.52 | 3.26 | 28.20 | 3.00 | 24.52 | 2.45 | 1.15 | 0.11 |
| 1st | lumbar vertebrae | 215 | 26.18 | 2.34 | 34.98 | 2.94 | 30.32 | 2.68 | 26.72 | 2.36 | 1.14 | 0.09 |
| 2nd | lumbar vertebrae | 233 | 26.57 | 2.76 | 36.09 | 3.31 | 30.88 | 2.72 | 27.55 | 2.83 | 1.13 | 0.11 |
| 3rd | lumbar vertebrae | 237 | 27.10 | 2.78 | 37.44 | 3.21 | 30.58 | 2.76 | 28.62 | 3.14 | 1.07 | 0.11 |
| 4th | lumbar vertebrae | 251 | 26.68 | 3.11 | 37.69 | 3.02 | 28.07 | 2.72 | 28.08 | 3.27 | 1.00 | 0.09 |
| 5th | lumbar vertebrae | 225 | 25.91 | 2.85 | 37.72 | 3.05 | 26.34 | 2.54 | 27.83 | 3.37 | 0.95 | 0.12 |

EXAMPLES

The present invention will now be further illustrated by, but is by no means limited to, the following Examples.

EXAMPLE 1

From the profile X-ray images of thoracic and lumbar vertebrae, with the eighth thoracic vertebrae and the third lumbar vertebrae as the center, of 50 to 75 year old women, the front brim length (d), central length (a), rear brim length (c), and vertebral body width (b) were measured for each vertebral body, and for the vertebral bodies classified by a physician as "no deformation", the average values ($\bar{x}$) and standard deviations ($\sigma$) for the

EXAMPLE 2

From the profile X-ray image of the thoracic and lumber vertebrae of a 70 year old osteoporosis patient (woman), the center length (a), vertebral body width (b), rear brim length (c), and front brim length (d) were measured for each vertebral body, and c/d, a/c and a/d were calculated. The results of the judgment of the presence of deformation of each vertebral body, and the type of change, are shown in Table 2. The judgment was made according to the judgment standard shown in Table 2. The same standards were also used in Examples 3 and 4.

TABLE 2

| Measurement site: | | a | b | c | d | c/d | a/c | a/d | Presence of deformation Type of deformation |
|---|---|---|---|---|---|---|---|---|---|
| Site: | | | | | | | | | |
| 5th | thoracic vertebrae | 13.5 | 28.8 | 20.6 | 15.9 | 1.30 | 0.65 | 0.85 | Nor deformation |
| 6th | thoracic vertebrae | 13.1 | 33.3 | 22.0 | 13.5 | 1.63 | 0.60 | 0.97 | Type I |
| 7th | thoracic vertebrae | 13.3 | 36.5 | 21.3 | 17.1 | 1.25 | 0.63 | 0.78 | Type II |
| 8th | thoracic vertebrae | 12.9 | 38.2 | 21.8 | 13.2 | 1.64 | 0.59 | 0.97 | Type I |
| 9th | thoracic vertebrae | 21.3 | 35.9 | 23.8 | 22.5 | 1.05 | 0.90 | 0.95 | No deformation |
| 10th | thoracic vertebrae | 17.8 | 38.5 | 23.8 | 21.8 | 1.09 | 0.75 | 0.82 | " |
| 11th | thoracic vertebrae | 15.2 | 38.2 | 25.8 | 16.8 | 1.53 | 0.59 | 0.91 | Type I |
| 12th | thoracic vertebrae | 20.1 | 38.7 | 29.1 | 16.9 | 1.73 | 0.69 | 1.19 | Type I |

TABLE 2-continued

| Measurement site: | a | b | c | d | c/d | a/c | a/d | Presence of deformation Type of deformation |
|---|---|---|---|---|---|---|---|---|
| 1st lumbar vertebrae | 12.7 | 40.4 | 27.3 | 17.8 | 1.53 | 0.46 | 0.71 | Type I |
| 2nd lumbar vertebrae | 18.7 | 40.8 | 27.9 | 22.0 | 1.27 | 0.67 | 0.85 | No deformation |
| 3rd lumbar vertebrae | 13.7 | 45.4 | 28.1 | 25.2 | 1.11 | 0.49 | 0.54 | Type II |
| 4th lumbar vertebrae | 17.2 | 42.4 | 26.5 | 31.2 | 0.85 | 0.65 | 0.55 | Type II |
| 5th lumbar vertebrae | 21.6 | 42.5 | 23.7 | 23.8 | 1.00 | 0.91 | 0.91 | No deformation |

EXAMPLE 3

From the profile X-ray image, with the third lumbar vertebrae as the center, of ten osteoporosis patients (women) 59 to 76 year old, the central length (a), vertebral body width (b), rear brim length (c), and front brim length (d) of the third lumber vertebrae were measured and c/d, a/c, and a/d were calculated. The results of the judgment of the presence of deformation, and the type of deformation, are shown in Table 3.

TABLE 3

| Measurement site: | a | b | c | d | c/d | a/c | a/d | Presence of deformation Type of deformation |
|---|---|---|---|---|---|---|---|---|
| Case (age): | | | | | | | | |
| 1 (59) | 31.4 | 38.6 | 38.0 | 34.2 | 1.11 | 0.83 | 0.92 | No deformation |
| 2 (63) | 28.0 | 40.2 | 33.3 | 32.4 | 1.03 | 0.84 | 0.86 | " |
| 3 (64) | 26.9 | 41.1 | 30.1 | 28.4 | 1.06 | 0.90 | 0.95 | " |
| 4 (66) | 18.3 | 41.0 | 31.6 | 21.4 | 1.47 | 0.58 | 0.85 | Type I |
| 5 (76) | 20.8 | 34.7 | 26.3 | 16.6 | 1.59 | 0.79 | 1.25 | " |
| 6 (65) | 21.2 | 37.6 | 32.7 | 17.4 | 1.88 | 0.65 | 1.22 | " |
| 7 (68) | 16.6 | 40.7 | 25.6 | 24.8 | 1.03 | 0.65 | 0.67 | Type II |
| 8 (66) | 20.4 | 41.4 | 29.6 | 30.9 | 0.96 | 0.69 | 0.66 | " |
| 9 (72) | 14.2 | 33.8 | 22.4 | 16.7 | 1.34 | 0.63 | 0.85 | Type III |
| 10 (62) | 21.2 | 31.9 | 23.8 | 21.7 | 1.09 | 0.89 | 0.97 | " |

EXAMPLE 4

From the profile X-ray image, with the eighth thoracic vertebrae and the third lumbar vertebrae as the center, of a 67 year old osteoporosis patient (woman), the center length (a), vertebral body width (b), rear brim length (c), and front brim length (d) from the sixth thoracic vertebrae to the fifth lumbar vertebrae were measured, and c/d, a/c, and a/d were calculated to judge the presence of deformation and the type of deformation. Six months later, the profile X-ray image of the same site was photographed again to judge the presence of deformation and the type of deformation according to the same method, and at the same time, the change in the ratios of a, b, c and d were calculated. The results are shown in Table 4.

TABLE 4

| | At initiation of experiment | | | | | | | | After 6 months | |
|---|---|---|---|---|---|---|---|---|---|---|
| | a | b | c | d | c/d | a/c | a/d | Type of deformation | a | b |
| 6th thoracic vertebrae | 15.8 | 30.8 | 23.2 | 15.9 | 1.46 | 0.68 | 0.99 | Type I | 16.7 | 29.0 |
| 7th thoracic vertebrae | 19.6 | 32.1 | 26.0 | 19.5 | 1.33 | 0.75 | 1.01 | No deformation | 19.6 | 33.8 |
| 8th thoracic vertebrae | 16.1 | 31.7 | 22.1 | 16.5 | 1.37 | 0.73 | 0.98 | No deformation | 14.7 | 32.7 |
| 9th thoracic vertebrae | 21.6 | 35.2 | 26.5 | 23.6 | 1.12 | 0.82 | 0.92 | No deformation | 19.9 | 36.0 |
| 10th thoracic vertebrae | 16.6 | 38.1 | 23.6 | 14.4 | 1.63 | 0.70 | 1.15 | Type I | 14.0 | 35.2 |
| 11th thoracic vertebrae | 24.2 | 37.8 | 29.1 | 25.4 | 1.15 | 0.83 | 0.95 | No deformation | 24.1 | 36.0 |
| 12th thoracic vertebrae | 26.3 | 37.8 | 31.3 | 27.5 | 1.14 | 0.84 | 0.96 | No deformation | 25.9 | 39.3 |
| 1st lumbar vertebrae | 27.5 | 35.1 | 33.3 | 28.1 | 1.19 | 0.82 | 0.98 | No deformation | 22.9 | 34.6 |
| 2nd lumbar vertebrae | 24.0 | 38.7 | 30.4 | 26.8 | 1.14 | 0.79 | 0.89 | No deformation | 20.0 | 35.6 |
| 3rd lumbar vertebrae | 14.3 | 41.6 | 21.4 | 20.7 | 1.03 | 0.67 | 0.69 | Type III | 9.1 | 39.8 |
| 4th lumbar vertebrae | 19.0 | 40.0 | 29.1 | 22.1 | 1.32 | 0.65 | 0.86 | No deformation | 19.2 | 36.4 |

TABLE 4-continued

| | | | | | | | | | | |
|---|---|---|---|---|---|---|---|---|---|---|
| 5th | lumbar vertebrae | 19.3 | 38.4 | 26.4 | 26.3 | 1.00 | 0.73 | 0.73 | Type II | 18.6 | 38.4 |

After 6 months

| | | c | d | c/d | a/c | a/d | Type of deformation | Change in ratio (%) | | | |
|---|---|---|---|---|---|---|---|---|---|---|---|
| | | | | | | | | a | b | c | d |
| 6th | thoracic vertebrae | 22.4 | 15.0 | 1.49 | 0.74 | 1.11 | Type I | 105 | 94 | 96 | 94 |
| 7th | thoracic vertebrae | 22.3 | 17.3 | 1.29 | 0.88 | 1.14 | No deformation | 100 | 105 | 85 | 88 |
| 8th | thoracic vertebrae | 21.9 | 16.3 | 1.34 | 0.67 | 0.90 | No deformation | 91 | 103 | 99 | 98 |
| 9th | thoracic vertebrae | 24.9 | 22.2 | 1.12 | 0.80 | 0.89 | No deformation | 91 | 102 | 94 | 94 |
| 10th | thoracic vertebrae | 22.9 | 14.5 | 1.58 | 0.61 | 0.97 | Type I | 84 | 92 | 97 | 100 |
| 11th | thoracic vertebrae | 28.6 | 25.0 | 1.14 | 0.84 | 0.96 | No deformation | 99 | 95 | 98 | 98 |
| 12th | thoracic vertebrae | 30.8 | 26.9 | 1.15 | 0.84 | 0.96 | No deformation | 98 | 103 | 98 | 97 |
| 1st | lumbar vertebrae | 31.8 | 26.4 | 1.21 | 0.72 | 0.87 | No deformation | 83 | 98 | 95 | 94 |
| 2nd | lumbar vertebrae | 23.6 | 20.8 | 1.13 | 0.85 | 0.96 | Type III | 83 | 92 | 77 | 77 |
| 3rd | lumbar vertebrae | 21.1 | 20.3 | 0.87 | 0.43 | 0.44 | " | 63 | 95 | 98 | 98 |
| 4th | lumbar vertebrae | 27.2 | 22.6 | 1.20 | 0.71 | 0.85 | No deformation | 101 | 91 | 93 | 102 |
| 5th | lumbar vertebrae | 26.4 | 25.4 | 1.04 | 0.70 | 0.73 | Type II | 96 | 99 | 100 | 96 |

The second lumbar vertebrae changed from a "no deformation" classification to a type III (flat vertebrae) within six months.

Although not showing a clear deformation, the conditions of the front brim and rear brim of the seventh thoracic vertebrae, and the center of the tenth thoracic vertebrae, tend to have worsened. Also, the conditions of the centers of the tenth thoracic vertebrae and the third lumbar vertebrae had further worsened.

On the other hand, substantially no change has occurred in the sixth, eighth, ninth, eleventh, and twelfth thoracic vertebrae, or in the fourth and fifth lumbar vertebrae.

EXAMPLE 5

For 186 vertebral bodies, including 6 vertebral bodies judged as wedge-shaped vertebrae, 25 vertebral bodies judged as fish vertebrae, eight vertebral bodies judged as flat vertebrae and 147 vertebral bodies judged as "no deformation" according to visual observation by a physician of a profile X-ray image, with the third lumbar vertebrae as the center, of osteoporosis patients (women), eight points of 1 to 8 shown in FIG. 4 were input through a digitizer into a computer to measure the central length (a), vertebral body width (b), rear brim length (c), and front brim length (d), and calculation was performed by a computer by inputting the above a, b, c, and d into a multivariate discriminant analytical program in the BMD multivariate analytical program of IBM Co. to obtain the coefficients and constants of the discriminant formula as shown in Table 5.

TABLE 5

| FUNCTION | 1 (wedge-shaped vertebrae) | 2 (fish vertebrae) | 3 (flat vertebrae) | 4 (no deformation) |
|---|---|---|---|---|
| COEFFICIENT | | | | |
| 1 (a) | 1.41660 | 0.14656 | −0.19733 | 1.94241 |
| 2 (b) | 3.31142 | 3.63664 | 3.37930 | 3.51934 |
| 3 (c) | 2.39311 | 1.77030 | 1.42894 | 1.43377 |
| 4 (d) | −0.73812 | 1.23660 | 1.18794 | 0.60223 |
| CONSTANT | −100.52945 | −114.00328 | −89.05205 | −123.11888 |

The discriminant value for each vertebral body was calculated by substituting the measured values of a, b, c, and d, into the above four discriminant formulae, and the type having the maximum numerical value was judged to be the vertebral body deformation type.

The coincidence of the vertebral body deformation type thus judged according to the discriminant formula with the vertebral body deformation type according to the physician's judgment is shown in Table 6, indicating a good coincidence between both judgments. The coincidence ratio of the respective types is 94.6%.

TABLE 6

| Discriminant analysis: | Wedge-shaped vertebrae | Fish vertebrae | Flat vertebrae | No deformation | Total | Coincidence ratio (%) |
|---|---|---|---|---|---|---|
| Physician's judgments: | | | | | | |
| Wedge-shaped vertebrae | 6 | 0 | 0 | 0 | 6 | 100.0 |

TABLE 6-continued

| Discriminant analysis: | Wedge-shaped vertebrae | Fish vertebrae | Flat vertebrae | No deformation | Total | Coincidence ratio (%) |
|---|---|---|---|---|---|---|
| Fish vertebrae | 0 | 23 | 2 | 0 | 25 | 92.0 |
| Flat vertebrae | 0 | 1 | ⑦ | 0 | 8 | 87.2 |
| No deformation | 2 | 1 | 0 | 140 | 147 | 95.2 |

The mark ○ shows the number of vertebral bodies for which both judgments coincide.

EXAMPLE 6

From a profile X-ray image, with the third lumbar vertebrae as the center, of 10 osteoporosis patients (women), the central length (a), vertebral body width (b), rear brim length (c), and front brim length (d) of the third lumbar vertebrae were measured and substituted in the discriminant formula determined in Example 5 (coefficients and constants are shown in Table 5) to calculate the respective discriminant values, and the type having the maximum numerical value was judged to be the vertebral body deformation type. The results are shown in Table 7.

lected, and the central length (a), vertebral width (b), rear brim length (c), and front brim length (d) of each vertebral body were measured as in Example 5, and in addition, the c/d was calculated.

For discriminating wedge-shaped vertebrae from "no deformation" with one variate of c/d, the value of c/d for each vertebral body was input to the one variate discriminant analytical program in the BMD multivariate analytical program of IBM Co. to obtain the discriminant values shown in Table 8. The coincidence with the physicians judgment when discrimination was made between wedge-shaped vertebrae and "no deformation" by use of these discriminant values is shown in

TABLE 7

| | Vertebral body measured values (mm) | | | | Discriminant values | | | | Deformation type |
|---|---|---|---|---|---|---|---|---|---|
| No. | a | b | c | d | Wedge-shaped vertebrae | Fish vertebrae | Flat vertebrae | No deformation | |
| 1 | 27.0 | 37.8 | 31.6 | 27.3 | 118.36 | 117.12 | 110.94 | 124.11 | No deformation |
| 2 | 27.5 | 33.4 | 32.6 | 28.1 | 106.30 | 103.95 | 98.35 | 115.51 | No deformation |
| 3 | 15.9 | 40.2 | 26.0 | 17.0 | 104.79 | 101.57 | 101.01 | 96.76 | Wedge-shaped vertebrae |
| 4 | 16.9 | 35.2 | 28.2 | 15.6 | 95.94 | 85.70 | 85.39 | 83.42 | Wedge-shaped vertebrae |
| 5 | 20.5 | 40.3 | 30.5 | 20.0 | 120.19 | 114.28 | 110.43 | 114.30 | Wedge-shaped vertebrae |
| 6 | 19.6 | 38.6 | 28.1 | 26.9 | 102.45 | 112.25 | 109.63 | 107.29 | Fish vertebrae |
| 7 | 20.8 | 36.9 | 28.7 | 30.0 | 97.67 | 111.14 | 108.19 | 106.36 | Fish vertebrae |
| 8 | 21.6 | 32.6 | 30.8 | 30.8 | 89.00 | 100.33 | 97.45 | 96.28 | Fish vertebrae |
| 9 | 13.2 | 34.0 | 21.3 | 17.3 | 68.96 | 70.68 | 74.23 | 63.14 | Flat vertebrae |
| 10 | 18.8 | 31.0 | 21.8 | 21.5 | 65.05 | 66.67 | 68.69 | 66.70 | Flat vertebrae |

EXAMPLE 7

From vertebral body profile X-ray images with the eighth thoracic vertebrae and the third thoracic vertebrae as the centers thereof, respectively, according to a physician's judgment, as shown in Table 8, from the sixth thoracic vertebrae to the third thoracic vertebrae, 257 vertebral bodies of wedge-shaped vertebrae and 2,157 vertebral bodies of "no deformation" were se- Table 8. For all vertebral bodies, the coincidence ratio of "no deformation" was 98.15%, and the coincidence ratio of wedge-shaped vertebrae 87.16%, thus giving good results.

TABLE 8

| | Number of vertebral bodies used for discrimination | | Discriminant c/d value according to discriminant function | Coincidence with physician's judgment | | | |
|---|---|---|---|---|---|---|---|
| | | | | Wedge-shaped vertebrae | | No deformation | |
| Site | Wedge-shaped vertebrae | No deformation | | Coincidence number | Coincidence ratio (%) | Coincidence number | Coincidence ratio (%) |
| Th 6 | 14 | 209 | 1.456 | 11 | 78.57 | 208 | 99.52 |
| Th 7 | 22 | 205 | 1.422 | 18 | 81.82 | 204 | 99.51 |
| Th 8 | 25 | 206 | 1.399 | 21 | 84.00 | 204 | 99.03 |
| Th 9 | 19 | 217 | 1.388 | 18 | 94.74 | 212 | 97.70 |
| Th 10 | 9 | 228 | 1.420 | 6 | 66.67 | 226 | 99.12 |
| Th 11 | 30 | 214 | 1.422 | 22 | 73.33 | 207 | 96.73 |
| Th 12 | 55 | 193 | 1.363 | 51 | 92.73 | 186 | 96.37 |
| L 1 | 52 | 214 | 1.341 | 49 | 94.23 | 212 | 99.07 |
| L 2 | 25 | 238 | 1.406 | 23 | 92.00 | 229 | 96.22 |
| L 3 | 6 | 233 | 1.407 | 5 | 83.33 | 229 | 98.38 |
| Total/average | 257 | 2,157 | 1.402 | 224 | 87.16 | 2,117 | 98.15 |

Th: thoracic vertebrae
L: lumbar vertebrae

EXAMPLE 8

From the profile X-ray images, with the eighth thoracic vertebrae as the center, of 10 osteoporosis patients (women), as described in Example 5, the center length (a), vertebral body width (b), rear brim length (c), and front brim length (d) of the eighth thoracic vertebrae were measured, and in addition, the c/d was calculated. The results are shown in Table 9. Since these vertebral bodies were neither clearly fish vertebrae nor flat vertebrae, a discrimination between wedge-shaped vertebrae and "no deformation" by the c/d determined in Example 7 was conducted. The results are shown in the right hand column in Table 9.

TABLE 9

| No. | Vertebrae body measured values (mm) | | | | | Deformation type |
| --- | --- | --- | --- | --- | --- | --- |
|  | a | b | c | d | c/d |  |
| 1 | 20.0 | 22.5 | 24.7 | 16.5 | 1.50 | Wedge-shaped vertebrae |
| 2 | 21.6 | 30.2 | 24.4 | 21.3 | 1.14 | No deformation |
| 3 | 17.5 | 32.9 | 21.7 | 13.6 | 1.60 | Wedge-shaped vertebrae |
| 4 | 17.7 | 38.3 | 29.6 | 15.6 | 1.90 | Wedge-shaped vertebrae |
| 5 | 22.0 | 28.8 | 23.8 | 19.2 | 1.24 | No deformation |
| 6 | 12.9 | 38.2 | 21.8 | 13.2 | 1.64 | Wedge-shaped vertebrae |
| 7 | 21.0 | 28.3 | 24.5 | 21.2 | 1.15 | No deformation |
| 8 | 18.9 | 32.0 | 22.4 | 18.5 | 1.21 | " |
| 9 | 19.8 | 30.8 | 24.3 | 18.7 | 1.30 | " |
| 10 | 19.3 | 31.3 | 22.2 | 15.6 | 1.43 | Wedge-shaped vertebrae |

We claim:

1. A method for judging deformation of a vertebral body in a subject comprising the steps of:
   (i) measuring a central length (a), a rear brim length (c) and a front brim length (d) from a plurality of profile X-ray images obtained from vertebral bodies having substantially no deformation at a portion corresponding to a portion of said vertebral body to be judged, storing the measurements in a memory, and determining values of c/d, a/c and a/d, the average values $\bar{c}$ and $\bar{d}$ of the rear brim lengths (c) and front brim lengths (d), respectively, and the standard deviations $\sigma_c$ and $\sigma_d$ of the values c and d, respectively;
   (ii) measuring a, c, and d from a plurality of the profile X-ray images obtained from vertebral bodies having at least one deformation of a "wedge-shaped" vertebrae, and "inverse wedge-shaped" vertebrae, a "fish" vertebrae, and a "flat" vertebrae, storing the measurements in said memory, and determining values of c/d, a/c, a/d, and $\bar{c}$, $\bar{d}$, $\sigma_c$, and $\sigma_d$;
   (iii) preparing a judgment standard from the data obtained in steps (i) and (ii) for determining the "no deformation" vertebrae, "wedge-shaped" vertebrae, "inverse wedge-shaped" vertebrae, "fish" vertebrae, and "flat" vertebrae;
   (iv) measuring a, c, and d from a profile X-ray image of said vertebral body to be judged, storing the measurements in said memory, and determining c/d, a/c, and a/d; and
   (v) classifying deformation of said vertebral body to be judged from c/d in the case of "wedge-shaped", and "inverse wedge-shaped" vertebrae, from $\bar{c}$, $\bar{d}$, $\sigma_c$, $\sigma_d$, and c/d in the case of "flat" vertebrae, and from $\bar{c}$, $\bar{d}$, $\sigma_c$, $\sigma_d$, a/c, a/d, and c/d in the case of the "no deformation" and "fish" vertebrae, in order to diagnose deformation and to monitor the effect of therapy on said vertebral body to be judged;

wherein said step (v) is carried out according to the following sub-steps:
   (i) $c/d \geq \beta_1$ ... wedge-shaped vertebrae (or anterior wedge fracture)
   (ii) $c/d \leq \beta_2$ ... inverse wedge-shaped vertebrae (or inverse anterior wedge fracture)
   (iii) $c < \bar{c} - \beta_3 \sigma_c$, $d < \bar{d} - \beta_4 \sigma_d$, and $\beta_2 < c/d < \beta_1$ ... flat vertebrae (or compression fracture)
   (iv) $\beta_2 < c/d < \beta_1$, $a/c \leq \beta_5$, $a/d \leq \beta_6$ and, $c \geq \bar{c} - \beta_3 \sigma_c$ and/or $d \geq \bar{d} - \beta_4 \sigma_d$ ... fish vertebrae (or central biconcave fracture)
   (v) $\beta_2 < c/d < \beta_1$, $c \geq \bar{c} - \beta_3 \sigma_c$ and/or $d \geq \bar{d} - \beta_4 \sigma_d$, and $a/c > \beta_5$ and/or $a/d > \beta_6$ ... No deformation (or no fracture), wherein $\beta_1$ to $\beta_6$ are selected as follows: $1.25 \leq \beta_1 \leq 1.55$, $0.6 \leq \beta_2 \leq 0.8$, $1 \leq \beta_3 \leq 2.5$, $1 \leq \beta_4 \leq 2.5$, $0.65 \leq \beta_5 \leq 0.9$, and $0.65 \leq \beta_6 \leq 0.9$;
   and wherein $\beta_1$ to $\beta_6$ are $1.33 \leq \beta_1 \leq 1.5$, $0.65 \leq \beta_2 \leq 0.75$, $1.25 \leq \beta_3 \leq 2.25$, $1.25 \leq \beta_4 \leq 2.25$, $0.7 \leq \beta_5 \leq 0.85$, and $0.7 \leq \beta_6 \leq 0.85$.

2. A method as claimed in claim 1, wherein the measuring step is carried out by a rule means, a digitizer means, or a means for automatically measuring the lengths from image treatment by memorizing the X-ray image with an X-ray image automatic input means.

3. A method as claimed in claim 1 wherein classifying deformation of the vertebral body is carried out as follows:
   (i) $c/d \geq \beta_1$ ... wedge-shaped vertebrae (or anterior wedge fracture)
   (ii) $c/d \leq \beta_2$ ... inverse wedge-shaped vertebrae (or inverse anterior wedge fracture)
   (iii) $c < \bar{c} - \beta_3 \sigma_c$, $d < \bar{d} - \beta_4 \sigma_d$, and $\beta_2 < c/d < \beta_1$ ... flat vertebrae (or compression fracture)
   (iv) $\beta_2 < c/d < \beta_1$, $a/c \leq \beta_5$, $a/d \leq \beta_6$ and, $c \geq \bar{c} - \beta_3 \sigma_c$ and/or $d \geq \bar{d} - \beta_4 \sigma_d$ ... fish vertebrae (or central biconcave fracture)
   (v) $\beta_2 < c/d < \beta_1$, $c \geq \bar{c} - \beta_3 \sigma_c$ and/or $d \geq \bar{d} - \beta_4 \pi_d$, and $a/c > \beta_5$ and/or $a/d > \beta_6$ ... No deformation (or no fracture), wherein $\beta_1$ to $\beta_6$ are selected as follows: $1.25 \leq \beta_1 \leq 1.55$, $0.6 \leq \beta_2 \leq 0.8$, $1 \leq \beta_3 \leq 2.5$, $1 \leq \beta_4 \leq 2.5$, $0.65 \leq \beta_5 \leq 0.9$, and $0.65 \leq \beta_6 \leq 0.9$.

4. A method as claimed in claim 3, wherein $\beta_1$ is 1.4, $\beta_2$ is 0.7, $\beta_3$ is 2, $\beta_4$ is 1.5, $\beta_5$ is 0.8, and $\beta_6$ is 0.8.

5. A method as claimed in claim 3, wherein at least one of $\beta_1$ to $\beta_6$ are determined by a discriminant function capable of discriminating two groups with one or two variables by using two of a, b, c, and d or a ratio of at least two variables thereof, which are obtained by measuring at least five profile X-ray images in each of two types selected from four types, "wedge-shaped vertebrae", "fish vertebrae", "flat vertebrae", and "no deformation".

6. A method as claimed in claim 5, wherein $\beta_1$ is $z_5$ obtained by the following discriminant function using the ratio c/d derived from c and d, which are obtained by measuring at least five profile X-ray images in each of two types selected from "wedge-shaped vertebrae" and "no deformation":
   (i) When the standard deviation $\sigma_1$ of c/d at least five profile X-ray images of "wedge-type vertebrae" is substantially the same as the standard deviation $\sigma_2$ of c/d of at least five profile X-ray images of "no deformation", $$z_5 = \mu + \frac{\sigma^2}{\mu_1 - \mu_2} l_n \frac{\pi_2}{\pi_1}$$

wherein $\mu_1$ and $\mu_2$ are averages of c/d relating to the profile X-ray images of "wedge-shaped vertebrae" and "no deformation", respectively, $\pi_1$ and $\pi_2$ are numbers of the X-ray images of "wedge-type vertebrae" and "no deformation", respectively, $\mu$ is an average of $\mu_1$ and $\mu_2$, and $\sigma$ is an average of $\sigma_1$ and $\sigma_2$; and (ii) When $\sigma_1$ and $\sigma_2$ are substantially different, $$z_5 = \frac{-B \pm \sqrt{B^2 - 4 A \cdot C}}{2A}$$

wherein A, B and C are determined from the following equations:

$$A = \frac{1}{\sigma_2^2} - \frac{1}{\sigma_1^2}$$

$$B = -2\left(\frac{\mu_2}{\sigma_2^2} - \frac{\mu_1}{\sigma_1^2}\right)$$

$$C = \frac{\mu_2^2}{\sigma_2^2} - \frac{\mu_1^2}{\sigma_1^2} - 2 \cdot \log\left(\frac{\pi_2}{\pi_1}\right)$$

wherein $\mu_1$ and $\mu_2$ are averages of c/d relating to the profile X-ray images of "wedge-shaped vertebrae" and "no deformation", respectively, $\pi_1$ and $\pi_2$ are numbers of the X-ray images of "wedge-type vertebrae" and "no deformation", respectively.

7. An apparatus for judging deformation of a vertebral body of a subject comprising:
(i) input means for inputting at least two lengths of a central length (a), vertebral body width (b), rear brim length (c), and front brim length (d) from a profile X-ray image of a particular vertebral body to be judged;
(ii) arithmetic means for performing calculations to discriminate between at least two of the following types: "wedge-shaped" vertebrae, "inverse wedge-shaped" vertebrae, "fish" vertebrae, "flat" vertebrae, and "no deformation" vertebrae by using the above-mentioned input values;
(iii) means for discriminating the at least two types by using the calculation results;
(iv) means for inputting a discriminant standard derived from profile X-ray images having substantially no deformation and necessary for the calculation and discrimination; and
(v) output means for outputting the judgment result in order to diagnose deformation and to monitor the effect of therapy on said vertebral body to be judged, wherein said arithmetic means performs said calculations based on a central length, vertebral body width, rear brim length, and front brim length measured from profile X-ray images of respective vertebral bodies, corresponding to said particular vertebral body of said subject, from a plurality of other subjects, said vertebral bodies in said other subjects having substantially no deformation, wherein said arithmetic means determines c/d, a/c, and a/d, said means for inputting a discriminant standard inputs a discriminating standard for $\bar{c}$, $\bar{d}$, $\sigma_c$, $\sigma_d$, and $\beta_1$ to $\beta_6$, (where $\bar{c}$, $\bar{d}$, are average values of c and d, respectively, $\sigma_c$, $\sigma_d$, are standard deviations of c and d, respectively, and $\beta_1$ to $\beta_6$ are indices) and said discriminating means is based on the following standards:
(i) $c/d \geq \beta_1$ ... "wedge-shaped vertebrae"
(ii) $c/d \leq \beta_2$ ... "inverse wedge-shaped vertebrae"
(iii) $c < \bar{c} - \beta_3 \sigma_c$, $d < -\beta_4 \sigma_d$, and $\beta_2 < c/d \beta_1$ ... "flat vertebrae"
(iv) $\beta_2 < c/d < \beta_1$, $a/c \leq \beta_5$, $a/d \leq \beta_6$ and, $c \geq \bar{c} - \beta_3 \sigma_c$ and/or $d \geq \bar{d} - \beta_4 \sigma_d$ ... "fish vertebrae"
(v) $\beta_2 < c/d < \beta_1$, $c \geq \bar{c} - \beta_3 \sigma_c$ and/or $d \geq \bar{d} - \beta_4 \sigma_d$, and $a/c > \beta_5$ and/or $a/d > \beta_6$ ... "no deformation" wherein $\beta_1$ to $\beta_6$ are $1.25 \leq \beta_1 \leq 1.55$, $0.6 \leq \beta_2 \leq 0.8$, $1 \leq \beta_3 \leq 2.5$, $1 \leq \beta_4 \leq 2.5$, $0.65 \leq \beta_5 \leq 0.9$, and $0.65 \leq \beta_6 \leq 0.9$.

8. An apparatus for judging deformation of a vertebral body as claimed in claim 7, wherein a table is prepared based on said at least two values, the discriminant standard, said judgment result.

9. An apparatus for judging deformation of a vertebral body of a subject comprising:
(i) input means for inputting at least two of the following values: central length (a), vertebral body width (b), rear rim length (c), and front brim length (d) from a profile X-ray image of a particular vertebral body to be judged;
(ii) arithmetic means for performing calculations to discriminate between at least two of the following types: "wedge-shaped" vertebrae, "inverse wedge-shaped" vertebrae, "fish" vertebrae, "flat" vertebrae, and "no deformation" vertebrae by using the above-mentioned input values;
(iii) means for discriminating the at least two types by using the calculations results;
(iv) means for inputting a discriminant mathematical function based on measured values from profile X-ray images of deformed vertebral bodies and on measured values from profile X-ray images having substantially no deformation and necessary for the calculation and discrimination; and
(v) output means for outputting the judgment result in order to diagnose deformation and to monitor the effect of therapy on said vertebral body to be judged, wherein said arithmetic means performs said calculations based on a central length, vertebral body width, rear brim length, and front brim length measured from profile X-ray images of vertebral bodies, corresponding to said particular vertebral body of said subject, from a plurality of other subjects, respectively, said vertebral bodies in said other subjects having at least two of the following respective deformation types: "wedge-shaped" vertebrae, "flat" vertebrae, "fish" vertebrae, and "no deformation" vertebrae, wherein said arithmetic means is connected with means for inputting a discriminant mathematical function for inputting the discriminant function and calculates discriminating values representing deformation by using the discriminant mathematical function, whereby the type of the vertebral body to be judged is determined according to the type corresponding to a maximum discriminating value, and wherein said discriminant mathematical function judges whether the vertebral body to be judged is a "wedge-shaped" vertebrae, "fish" vertebrae, "flat vertebrae" and "no deformation" from four one-dimensional formulas containing four unknowns a, b, c and d.

10. An apparatus for judging deformation of a vertebral body as claimed in claim 9, wherein a table is prepared based on the at least two values, the discriminant mathematical function, and the judgment result.

11. A method for judging deformation of a vertebral body in a subject comprising the steps of:
   (i) obtaining at least two indices by measuring a central length (a), vertebral body width (b), rear brim length (c), and front brim length (d) from a profile X-ray image of a vertebral body to be judged, and storing said at least two indices in a memory;
   (ii) analysing said indices by a discriminant function obtained by using at least two indices measured from profile X-ray images of at least one other subject having at least two of the following deformation types: "wedge-shaped" vertebrae, "flat" vertebrae, "fish" vertebrae, and "no deformation";
   (iii) classifying a deformation of said vertebral body to be judged from the results of said analysing step, in order to diagnose the condition of and to monitor the effect of therapy on said vertebral body to be judged;
   wherein said discriminant function is obtained by using indices a, b, c and d measured from at least five profile X-ray images of other subjects in each of said four types of vertebrae, and is capable of discriminating said four types of the vertebral body using indices a, b, c and d, said discriminant function being represented by the following formulae, where the vertebral body is judged from the maximum value of $z_1$ to $z_4$:

$$z_1 = a_{10} + a_{11}x_1 + a_{12}x_2 + a_{13}x_3 + a_{14}x_4$$

$$z_2 = a_{20} + a_{21}x_1 + a_{22}x_2 + a_{23}x_3 + a_{24}x_4$$

$$z_3 = a_{30} + a_{31}x_1 + a_{32}x_2 + a_{33}x_3 + a_{34}x_4$$

$$z_4 = a_{40} + a_{41}x_1 + a_{42}x_2 + a_{43}x_3 + a_{44}x_4$$

wherein $z_1$, $z_2$, $z_3$, and $z_4$ are discriminant values of "wedge-shaped vertebrae", "fish vertebrae", "flat vertebrae", and "no deformation", respectively, $x_1$, $x_2$, $x_3$, and $x_4$ are variables corresponding to a central length, vertebral body width, rear brim length, and front brim length, respectively, of the vertebrae to be judged, $a_{10}$, $a_{20}$, $a_{30}$, and $a_{40}$ are constants, and $a_{11}$ to $a_{44}$ are coefficients.

12. A method as claimed in claim 11, wherein the measurement is carried out by a rule means, a digitizer means, or a means for automatically measuring the lengths from image treatment by memorizing the X-ray image with an X-ray image automatic input means.

13. A method for judging deformation of a vertebral body in a subject as claimed in claim 11, wherein a table is prepared based on the measurements, the analysis, and the discriminant function.

14. A method for judging deformation of a vertebral body in a subject comprising the steps of:
   (i) obtaining at least two indices by measuring a central length (a), vertebral body width (b), rear brim length (c), and front brim length (d) from a profile X-ray image on a vertebral body to be judged, and storing said at least two indices in a memory;
   (ii) analysing said indices by a discriminant function obtained by using at least two indices measured from profile X-ray images of at least one other subject having at least two of the following deformation types: "wedge-shaped" vertebrae, "flat" vertebrae, "fish" vertebrae, and "no deformation";
   (iii) classifying a deformation of said vertebral body to be judged from the results of said analysing step, in order to diagnose the condition of and to monitor the effect of therapy on said vertebral body to be judged;
   wherein said discriminant function is derived from at least two indices obtained by measuring a, b, c, and d from at least five profile X-ray images in each of two of said four types, and wherein said four types of vertebral body are capable of being identified and distinguished using as variables said at least two measured values or ratios of said at least two measured values;
   said discriminant function being represented by the following formula in which the ratio (c/d) of c and d is measured from at least five profile X-ray images in each of said two of said four types, a ratio value (c/d) of less than $z_5$ obtained from the vertebral body to be judged being judged as "no deformation", and a ratio value (c/d) equal to or larger than $z_5$ being judged as "wedge-shaped vertebrae":
   (i) when the standard deviation $\sigma_1$ of c/d of at least five profile X-ray images of "wedge-shaped vertebrae" is substantially the same as the standard deviation $\sigma_2$ of c/d of at least five profile X-ray images of "no deformation", $$z_5 = \mu + \frac{\sigma^2}{\mu_1 - \mu_2} \ln\left(\frac{\pi_2}{\pi_1}\right)$$

wherein $\mu_1$ and $\mu_2$ are averages of c/d relating to the profile X-ray images of "wedge-shaped vertebrae" and "no deformation", representatively, $\mu$ is an average of $\mu_1$ and $\mu_2$, and $\sigma$ is an average of $\sigma_1$ and $\sigma_2$; and
   (ii) when $\sigma_1$ and $\sigma_2$ are substantially different, $$z_5 = \frac{-B \leq \sqrt{B^2 - 4A \cdot C}}{2A}$$

wherein A, B and C are determined from the following equations:

$$A = \frac{1}{\sigma_2^2} - \frac{1}{\sigma_1^2}$$

$$B = -2\left(\frac{\mu_2}{\sigma_2^2} - \frac{\mu_1}{\sigma_1^2}\right)$$

$$C = \frac{\mu_2^2}{\sigma_2^2} - \frac{\mu_1^2}{\sigma_1^2} - 2 \cdot \log\left(\frac{\pi_2}{\pi_1}\right)$$

wherein $\pi_1$ and $\pi_2$ are the numbers of the X-ray images of "wedge-type vertebrae" and "no deformation", respectively.

15. A method as claimed in claim 14, wherein the measurement is carried out by a rule means, a digitizer means, or a means for automatically measuring the lengths from image treatment by memorizing the X-ray image with an X-ray image automatic input means.

16. A method for judging information of a vertebral body in a subject as claimed in claim 14, wherein a table is prepared based on the measurements, the analysis, and the discriminant function.

17. A method for judging deformation of a vertebral body in a subject comprising the steps of:

(i) measuring a central length (a), a rear brim length (c) and a front brim length (d) from a plurality of profile X-ray images obtained from vertebral bodies having substantially no deformation at a portion corresponding to a portion of said vertebral body to be judged, storing the measurements in a memory, and determining values of c/d, a/c and a/d, the average values $\bar{c}$ and $\bar{d}$ of the rear brim lengths (c) and front brim lengths (d), respectively, and the standard deviations $\sigma_c$ and $\sigma_d$ of the values c and d, respectively;

(ii) measuring a, c and d from a plurality of the profile X-ray images obtained from vertebral bodies having at least one deformation of a "wedge-shaped" vertebrae, and "inverse wedge-shaped" vertebrae, a "fish" vertebrae, and a "flat" vertebrae, storing the measurements in said memory, and determining values of c/d, a/c, a/d, and $\bar{c}$, $\bar{d}$, $\sigma_c$, and $\sigma_d$;

(iii) preparing a judgment standard from the data obtained in steps (i) and (ii) for determining the "no deformation" vertebrae, "wedge-shaped" vertebrae, "inverse wedge-shaped" vertebrae, "fish" vertebrae, and "flat" vertebrae;

(iv) measuring a, c, and d from a profile X-ray image of said vertebral body to be judged, storing the measurements in said memory, and determining c/d, a/c, and a/d; and (v) classifying deformation of said vertebral body to be judged from the physical vertebral body measurements c/d in the case of "wedge-shaped", and "inverse wedge-shaped" vertebrae, from $\bar{c}$, $\bar{d}$, $\sigma_c$, $\sigma_d$, and c/d in the case of "flat" vertebrae, and from $\bar{c}$, $\bar{d}$, $\sigma_c$, $\sigma_d$, a/c, a/d, and c/d in the case of the "no deformation" and "fish" vertebrae, in order to diagnose deformation and to monitor the effect of therapy on said vertebral body to be judged;

wherein said step (v) is carried out according to the following sub-steps:

(i) $c/d \geq \beta_1$ . . . wedge-shaped vertebrae (or anterior wedge fracture)

(ii) $c/d \leq \beta_2$ . . . inverse wedge-shaped vertebrae (or inverse anterior wedge fracture)

(iii) $c < \bar{c} - \beta_3\sigma_c$, $d < \bar{d} - \beta_4\sigma_d$, and $\beta_2 < c/d < \beta_1$ . . . vertebrae (or compression fracture)

(iv) $\beta_2 < c/d < \beta_1$, $a/c \leq \beta_5$, $a/d \leq \beta_6$ and, $c \geq \bar{d} - \beta_3\sigma_c$ and/or $d \geq \bar{d} - \beta_4\sigma_d$ . . . fish vertebrae (or central biconcave fracture)

(v) $\beta_2 < c/d < \beta_1$, $c \geq \bar{c} - \beta_3\sigma_c$ and/or $d \geq \bar{d} - \beta_4\sigma_d$, and $a/c > \beta_5$ and/or $a/d > \beta_6$ . . . No deformation (or no fracture), wherein $\beta_1$ to $\beta_6$ are selected as follows: $1.25 \leq \beta_1 \leq 1.55$, $0.6 \leq \beta_2 \leq 0.8$, $1 \leq \beta_3 \leq 2.5$, $1 \leq \beta_4 \leq 2.5$, $0.65 \leq \beta_5 \leq 0.9$, and $0.65 \leq \beta_6 \leq 0.9$;

and wherein $\beta_1$ to $\beta_6$ are $1.33 \leq \beta_1 \leq 1.5$, $0.65 \leq \beta_2 \leq 0.75$, $1.25 \leq \beta_3 \leq 2.25$, $1.25 \leq \beta_4 \leq 2.25$, $0.7 \leq \beta_5 \leq 0.85$, and $0.7 \leq \beta_6 \leq 0.85$.

* * * * *